United States Patent
Young et al.

[11] Patent Number: 5,915,332
[45] Date of Patent: Jun. 29, 1999

[54] COMBINED SYSTEM FOR DETECTING ANIMAL'S MOTION AND ACTIVITY

[76] Inventors: Ming-Shing Young, No. 336, Kai Hsuan Road, Tainan; Yan-Chay Li, No. 1, Nung 4, Lane 247, Nan Kung Street, Yung Kang Shih, Tainan Hsien, both of Taiwan

[21] Appl. No.: 08/709,758
[22] Filed: Sep. 9, 1996
[51] Int. Cl.[6] .................................................. A01K 29/00
[52] U.S. Cl. ............................................................ 119/421
[58] Field of Search ................................... 119/421, 907, 119/174

[56] References Cited

U.S. PATENT DOCUMENTS

| | | | |
|---|---|---|---|
| 3,693,590 | 9/1972 | Bowers | 119/421 |
| 3,803,571 | 4/1974 | Luz | 119/421 |
| 4,574,734 | 3/1986 | Mandalaywala et al. | 119/421 |

*Primary Examiner*—Thomas Price
*Attorney, Agent, or Firm*—Morton J. Rosenberg; David I. Klein; Jun Y. Lee

[57] ABSTRACT

There is provided a system for automatically sensing the activities of an animal within a confined space. The system generally includes a containment assembly having top and side portions within which an animal may be confined. The system also includes an infrared light matrix subsystem for sensing the animal's position within the containment assembly relative to a first plane; an ultrasonic phase shift subsystem for sensing animal's position change within the containment assembly relative to a second plane; as well a decoding and interface circuit subsystems coupled to both the infrared light matrix and ultrasonic phase shift subsystems to perform the necessary decoding and input/output interface functions. The infrared light matrix subsystem is formed by a plurality of infrared transmitter and receiver pairs preferably attached to the side portions of the containment assembly and controlled by a single-chip microcomputer. The ultrasonic phase shift subsystem is formed by a plurality of ultrasonic transmitter and receiver pairs preferably attached to the top portion of the containment assembly which are also controlled by a single-chip microcomputer.

6 Claims, 24 Drawing Sheets

1

COMBINED SYSTEM FOR DETECTING ANIMAL'S MOTION AND ACTIVITY

BACKGROUND OF THE INVENTION

In animal motion activity measurement, the engineering techniques are usually adopted to measure the changes of animal motion activity in a limited space, but most of the developed automatic methods for animal activity measurement could not get the whole data of the animal motion activity patterns and tracks of movement at a time.

To record the animal's moving path is of considerable importance and is very useful for many applications in behavior and neurophysiological studies. From the moving path, many useful variables of motor behavior could be analyzed such as total distance traveled, average speed, rest time, turning, and pattern of movement. A number of automatic measuring systems have been developed and reported and also available commercially. Various detection methods were offered. These include the use of video camera and photocell methods. The video camera system, however, has some drawbacks; for example, measurement needs proper illumination and sharp contrast between animal and background is required. The photocell method used interrupt such as IR light beam for animal path detection.

SUMMARY OF THE INVENTION

The system of the present invention combines IR light matrix subsystem with ultrasonic phase shift subsystem. The IR light matrix subsystem is used to record the horizontal position of an animal inside a cage. In each direction (X, Y, or Z axis), twenty-four pairs of IR light transmitters and receivers are fixed on cage wall. Each transmitter and its corresponding receiver were fixed face by face along the same direction.

There is a cover above the acrylic cage. We upholstered the cover with sixteen ultrasonic transducer pairs, because the effective measured range of an ultrasonic pair was finite. In order to avoid the possible interferences among ultrasonic transducer's arrays this combined system only opened one pair of ultrasonic transducers at a time. In the other words, the ultrasonic pair which was just above the animal was started by a decoding circuit, and used to detect the animal minute activities. Specifically, we used the IR light matrix to detect the animal position and select a right one from the ultrasonic transducer's array to detect the animal's vertical motion activities. Finally, we transfered the collected data to the IBM PC/AT compatible personal computer through an input/output interface card for further processing.

BRIEF DESCRIPTION OF DRAWINGS

The invention will be better understood by reference to the accompanying drawings, wherein.

DETAILED DESCRIPTION OF THE PREFERRED EMBODIMENTS

Figure 6:
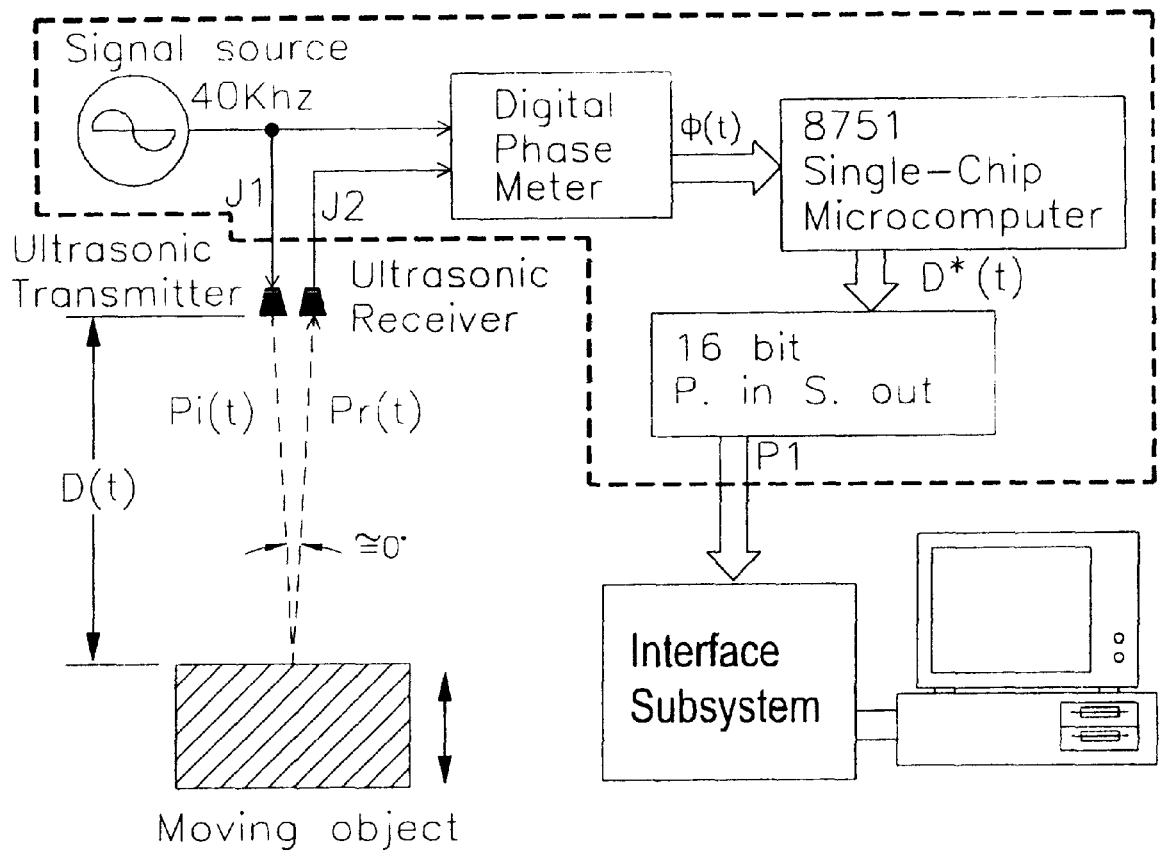
FIG. 6 is a functional block diagram of the ultrasonic motion measurement system in the preferred embodiment of the present invention.

FIG. 6 shows the block diagram of the ultrasonic subsystem for motion measurement. Two ultrasonic transducers, a transmitter and receiver, are attached together. For the moving object, the angle between incident ultrasonic wave Pi(t) and reflected wave Pr(t) is negligible. In operation, the ultrasonic transmitter will transmit Pi(t) and the ultrasonic receiver will simultaneously receive the ultrasound reflected by the object. An 8-bit digital phase meter was designed for detecting the phase difference between Pi(t) and Pr(t). The phase meter readout $\phi(t)$ is then sent to the 8751 single-chip microcomputer for further processing. If we ignore the Doppler effect (which will be discussed latter), the transmitted and received waves Pi(t) and Pr(t) are given by $$Pi(t)=Ai \cos (wt) \quad (1)$$

$$Pr(t)=Ar \cos (wt-2D(t)w/c) \quad (2)$$

where w is the angular frequency of the wave, c is the speed of sound, and D(t) is the distance between the object and ultrasonic transducer. The factor 2 in the Pr(t) function represents the round-trip path of the ultrasound. Therefore, the phase delay between the transmitted and received waves Pi(t) and Pr(t) is given by $$\phi(t)=(2\pi/\lambda)2D(t) \quad (3)$$

where $\lambda$ is the wavelength of ultrasound. The $\phi(t)$ in equation (3) represents the phase difference shift caused by D(t). Although the relationship between $\phi(t)$ and D(t) in equation (3) is linear, but when taking an actual measurement the phase detector will limit $\phi(t)$ to a value between 0 to $2\pi$.

Figure 7:
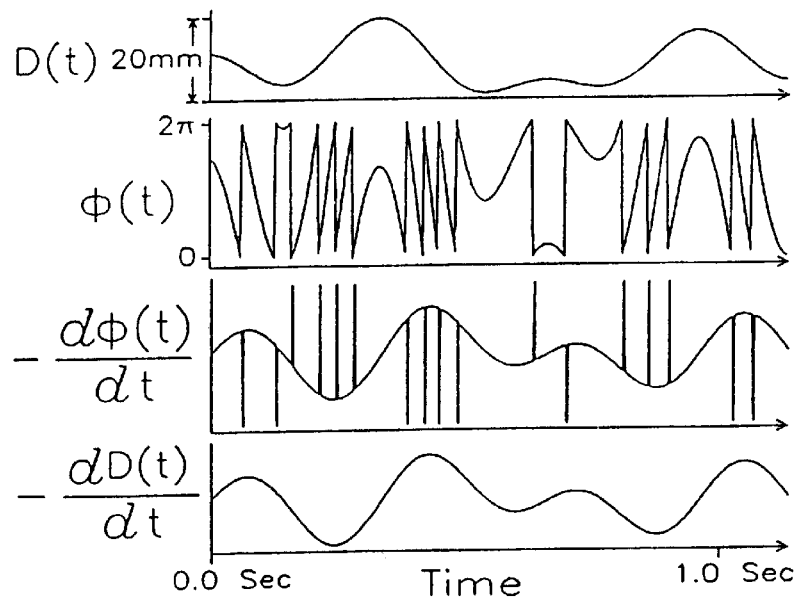
FIG. 7 is a graphic illustration of signal waveforms generated in the preferred embodiment of the present invention.

FIG. 7 shows the relationship of D(t) and $\phi(t)$. In our system, the frequency of the ultrasound is 40 Khz. The wave length $\lambda$ of the 40 Khz ultrasound is about 8.96 mm. When the object has a movement of 4.48 mm ($\lambda/2$), the $\phi(t)$ will have a variation of $2\pi$. A number of traditional phase measurement techniques for analyzing the phase difference between two signals can be used here. But these methods can only measure the phase difference shift from 0 to $2\pi$. Therefore, a 40 khz ultrasound signal can only have a maximum measurable range of 4.48 mm. Such a small maximum range greatly limits the use of these phase detection methods to measure object motion.

Figure 8:
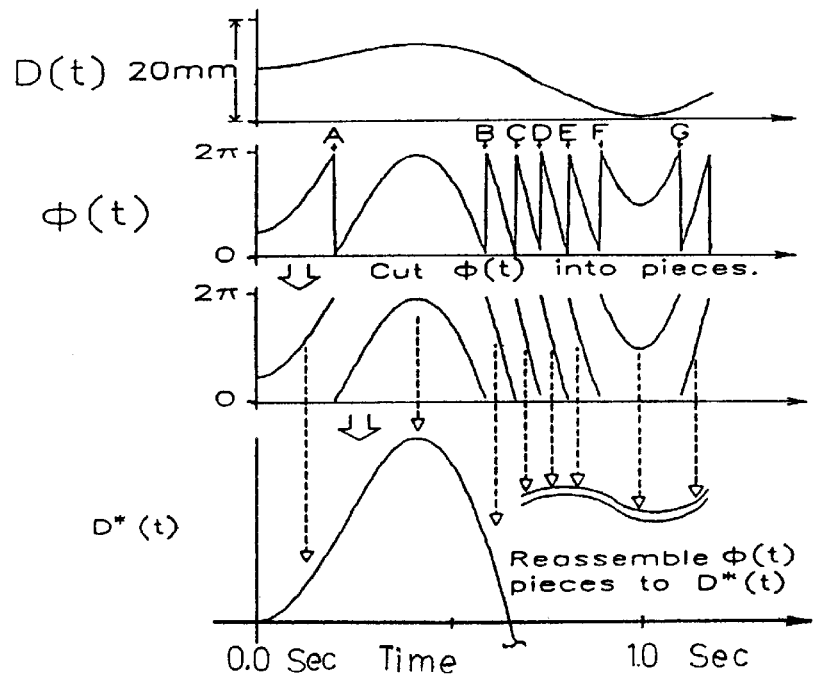
FIG. 8 is an illustrative diagram for illustrating the reconstruction of the motion function from the phase difference rate of change function in the preferred embodiment of the present invention.

Therefore, we have designed a method to overcome this limitation. In FIG. 8, the points A to G represent the situation where $\phi(t)$ has an abrupt change from 0 to $2\pi$ or $2\pi$ to 0. By analyzing $\phi(t)$ data and ignoring the abrupt change portion in $\phi(t)$ and reconstructing D(t) from $\phi(t)$, the limitation is overcome. FIG. 8 also shows the method to reconstruct D(t) from $\phi(t)$. The change of phase difference at each point is immediate so it can be separated from the normal phase change such as the phase change period between point A and B in FIG. 8. From equation (3), we know that $\phi(t)$ varies with D(t) linearly. Therefore, if we can cut $\phi(t)$ into pieces according to the abrupt change portions of the phase differences and reassemble them as D*(t) as shown in FIG. 8, we can obtain D(t) by multiplying D*(t) by a scaling factor. Thus, we conclude that if the phase cycle position A to G can be detected accurately we can easily cut $\phi(t)$ and reassemble D(t) from $\phi(t)$.

In FIG. 7, the d $\phi(t)$/dt curve represents the differentiation of $\phi(t)$ with time. By comparing the curves d$\phi(t)$/dt and $\phi(t)$, we can find that each impulse in d$\phi(t)$/dt is coincident with an abrupt change portion of $\phi(t)$. As $\phi(t)$ linearly varies with the D(t) function, d$\phi(t)$/dt will also have a linear relation with dD(t)/dt. The dD (t)/dt function represents the motion speed of the object and d$\phi(t)$/dt represents the varying rate of $\phi(t)$. However, from FIG. 7, we see that those impulses in d$\phi(t)$/dt do not appear in dD(t)/dt. Thus, it can be inferred that the velocity of an object is much slower than the rate of change of the phase difference of the ultrasonic signals. This is the key point in reconstructing D(t) from $\phi(t)$. The procedure for reconstructing D(t) can be simply described as follows.

Step 1: record $\phi(t)$'s change with time.
Step 2: differentiate $\phi(t)$ with time.
Step 3: ignove the impulses in d$\phi(t)$/dt by setting a threshold.
Step 4: integrate the result obtained from step 3 (d$\phi(t)$/dt without the impulses) with time.
Step 5: multiply the result obtained from step 4 by a scaling factor. The final result will be the D(t) function representing the object's motion.

The ultrasound frequency used in our system as shown in FIG. 6 is 40 Khz with a wavelength of 8.96 mm. The digital phase meter in our system has a resolution of 200 scales which represents a phase difference shift of $2\pi$. The 8751 single-chip microcomputer samples phase difference variation data at a rate of 10 Khz per second. That is, the 8751 will read the phase meter output every 100 $\mu$s. The output of the 8751 single-chip microcomputer is a 16-bit word data which represents the current position of the object. This output will be sent to the interface circuits. From equation (3), the ratio between object movement and phase meter readout is (8.96 mm/2)/200=0.0224 mm, so the theoretical motion measurement resolution of this system is 0.0224 mm (22.4 $\mu$m). For separating the abrupt change of the phase difference from $\phi(t)$ a threshold value of 150 was chosen as the check level in this system. For each sampling interval (100 $\mu$s), if the difference between the previous phase readout and the current readout is less than 150, the current readout of phase meter is recognized as the normal phase shift caused by the object moving, otherwise, it is an abrupt phase change point. Based on this algorithm, all the abrupt change points of the phase difference can be identified. The motion of the object can now be reconstructed by cutting the $\phi(t)$ waveform into pieces and reassembling them as the D*(t) waveform. However, the threshold value 150 will also limit the object's maximum measurable moving speed which is (150×0.00224 mm)/100 $\mu$s=336000 mm/s=336 m/s. But obviously, this speed limitation is impossible to achieve due to the Doppler effect.

After considering the Doppler effect caused by the moving object, the Pr(t) function in equation (2) will become $$Pr(t)=Ar \cos ((w+w_d)t-2D(t)(w+w_d)/c)=Ar \cos ((wt-2D(t)w/c)(w_dt-2D(t)w_d/c)) \quad (4)$$

where $w_d$ is the Doppler shift frequency and can be represented by $$w_d=2wV/c$$

where V is the velocity of object. The term $(w_dt-2D(t)w_d/c)$ in equation (4) is negligible only when $w_d$ is very small. As previously mentioned, the resolution of the digital phase meter is 200, therefore if the phase variance caused by the Doppler effect is less than $2\pi/200$, this effect can be ignored. This also means if $w_d$ is less than w/200 then the term $(w_d t-2D(t)w_d/c)$ in equation (4) is negligible. Now we can calculate the maximum measurable speed of the object from equation (5) as $$V=w_dc/2w=c/400=358.4/400=0.896(m/s).$$

The measurable motion amplitude in this system is determined by the output resolution. The 8751's output is originally set at 8000 H; therefore, the maximum measurable motion amplitude of an object is ±(32768×0.0224 mm)=±734.0032 mm.

DESCRIPTION OF PREFERRED EMBODIMENT

A combined system for detecting and analyzing animal activity comprising a housing, an infrared light matrix subsystem fitted to four sides the housing, an ultrasonic phase shift subsystem fitted to top side of the housing and decoding and interface circuits connected to a computer used for caculating the gathered data. The horizontal motion and track of the experiment subject animal are detected by infrared light, the conditions of how the infrared light is interrupted on the middle by the subject animal being varied as the animal moves. The decoding circuit decodes the data from the IR light matrix subsystem and starts an appropriate pair transmitter and receiver of the ultrasonic phase shift subsystem to detect vertical behavior change. The data from the ultrasonic phase shift subsystem is sent to the computer for calculation through the interface circuit.

Figure 1:
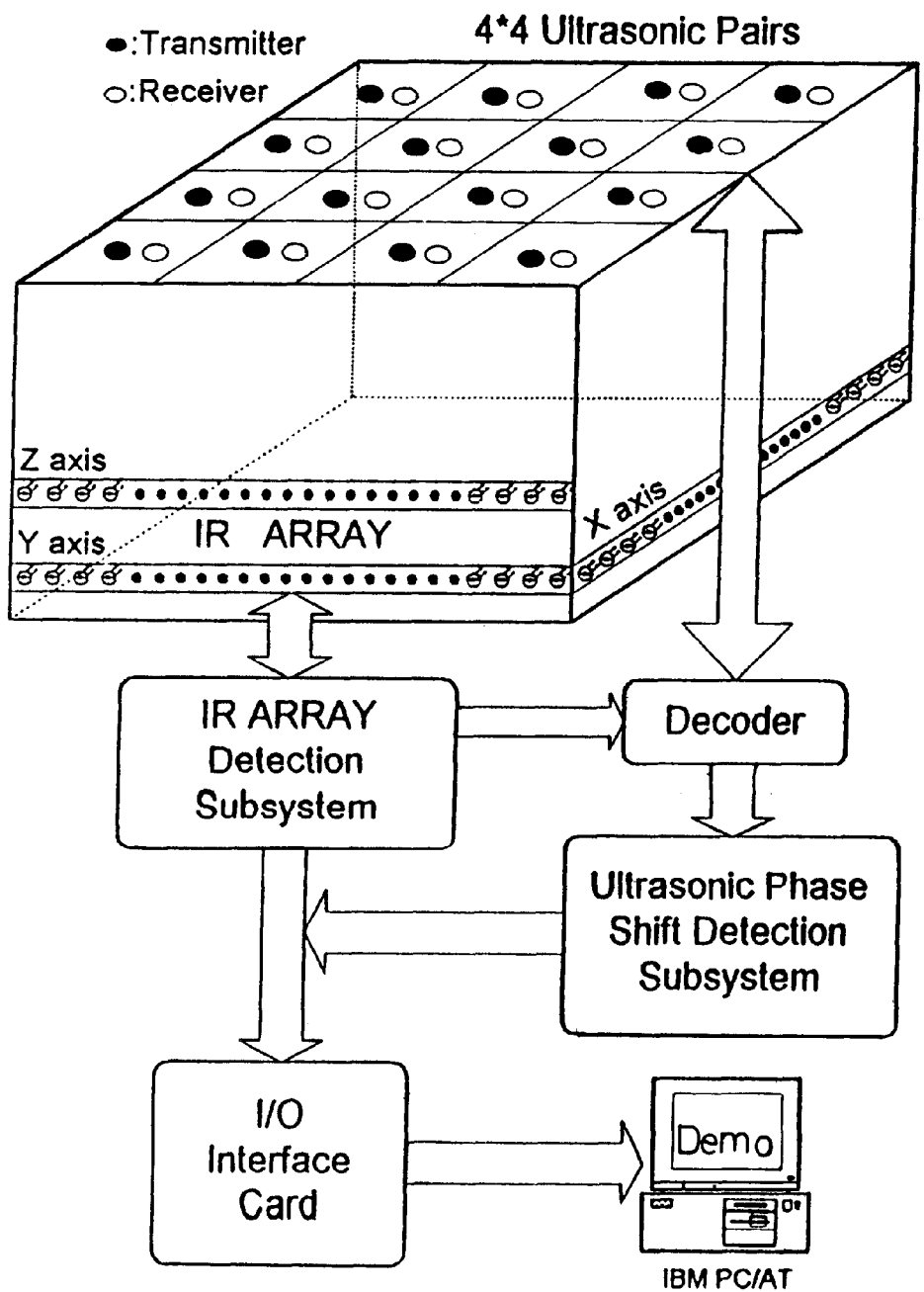
FIG. 1 is a functional schematic diagram illustrating a preferred embodiment of the present invention.
Figure 2:
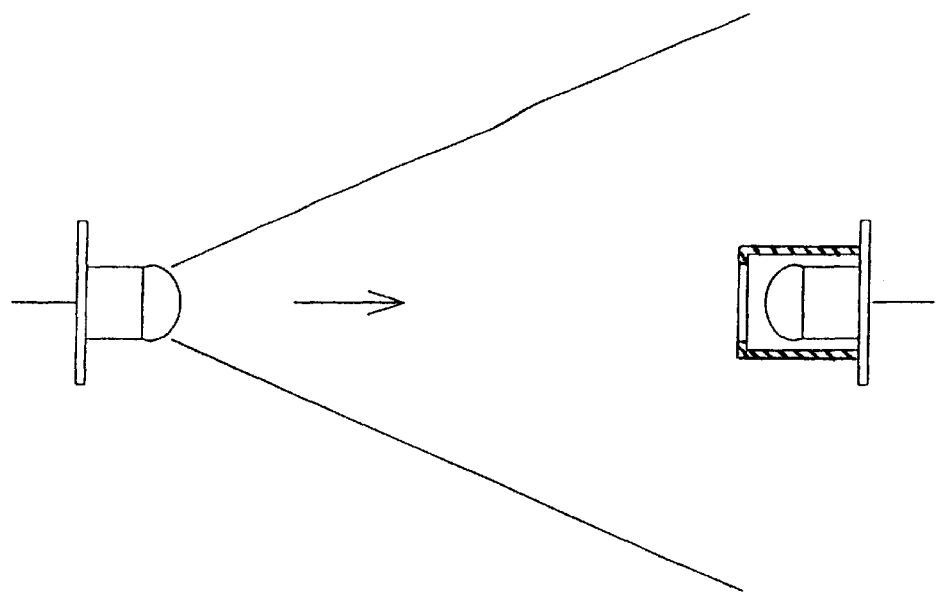
FIG. 2 is an elevational view, partially cut away of an infrared ray transmitter and receiver pair in the preferred embodiment of the present invention.
Figure 15:
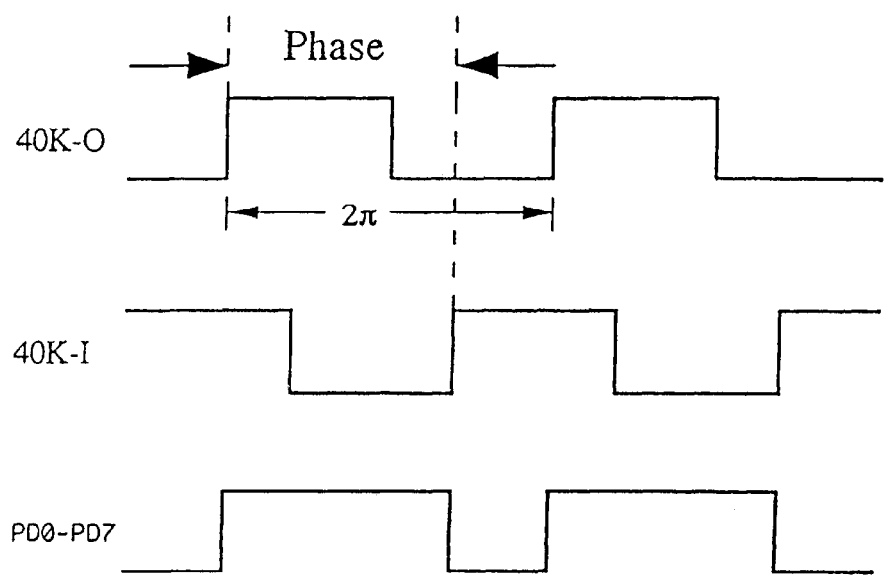
FIG. 15 is a series of timing diagrams of signals generated in the phase detection circuits in the preferred embodiment of the present invention.
Figure 3:
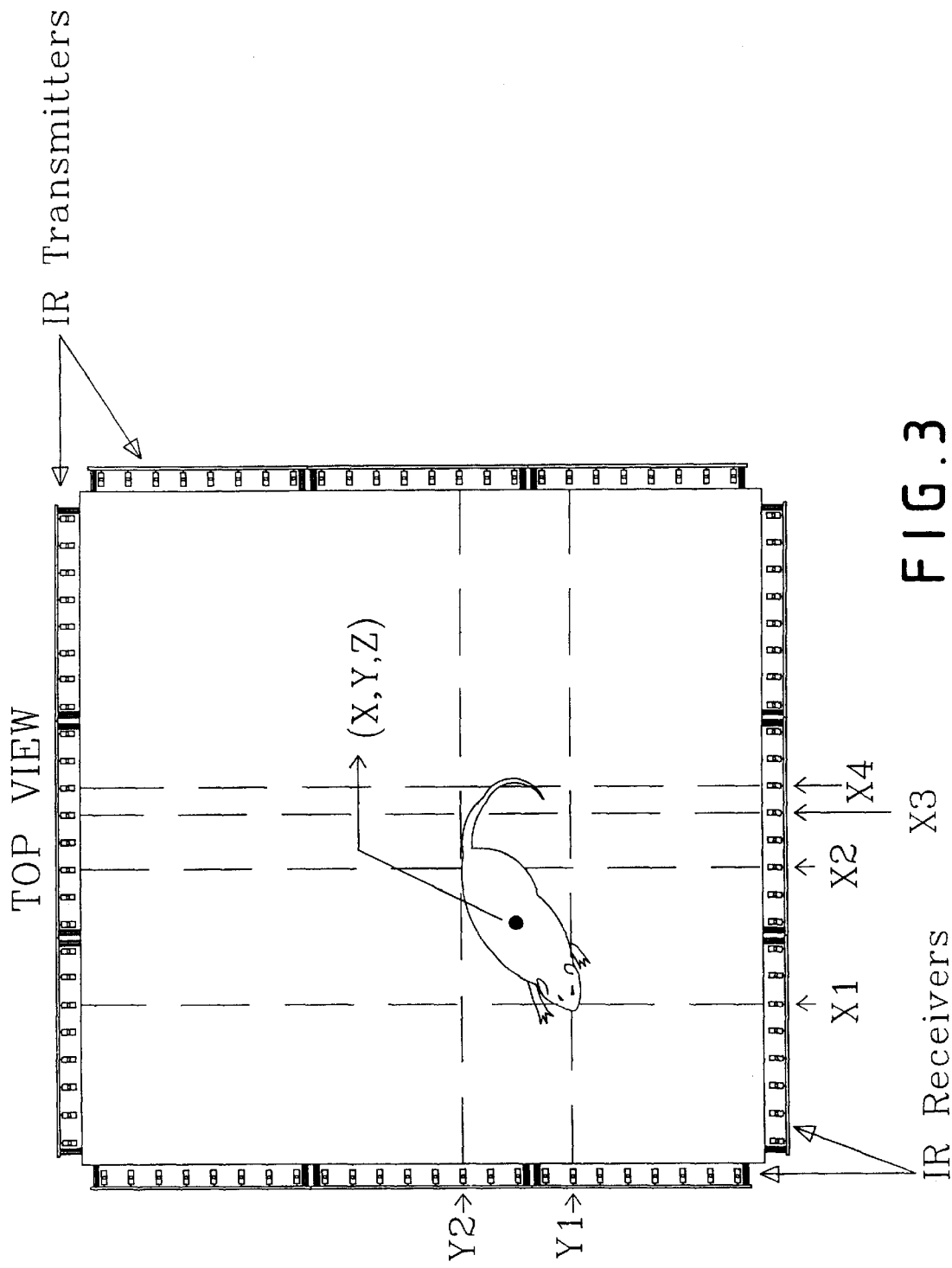
FIG. 3 is a cross-sectional plan view of the cage in the preferred embodiment of the present inventions

The IR light matrix subsystem, referring to FIG. 2, includes IR transmitter modules, IR receiver modules and 8751 single-chip microcomputer. In the infrared light matrix subsystem, an IR transmitter module is provided with eight IR light emitting diodes, while an IR receiver module is provided with eight photo transistors. Three IR transmitter modules are fitted on a first side of the cage and three IR receiver modules are fitted on the corresponding position on a second side opposing the first side to construct twenty-four pairs of IR light transmitters and receivers in X-axis. Twenty-four pairs of IR light transmitters and receivers in Y-axis are constructed in the same manner on two sides respectively adjacent to the first and second side of the cage. Twenty-four pairs of IR light transmitters and receivers in Z-axis are constructed also on the first and second side of the cage in the same manner ten centimeters above the X-axis. The relation between an IR light emitting diode and a photo transistor is shown in FIG. 3. The subsystem controller module is based on an 8751 single-chip microcomputer and connected to the transmitter module and receiver module. The 8751 single-chip microcomputer transmits the calculated coordinate data to the decoding and interface circuits.

Figure 16:
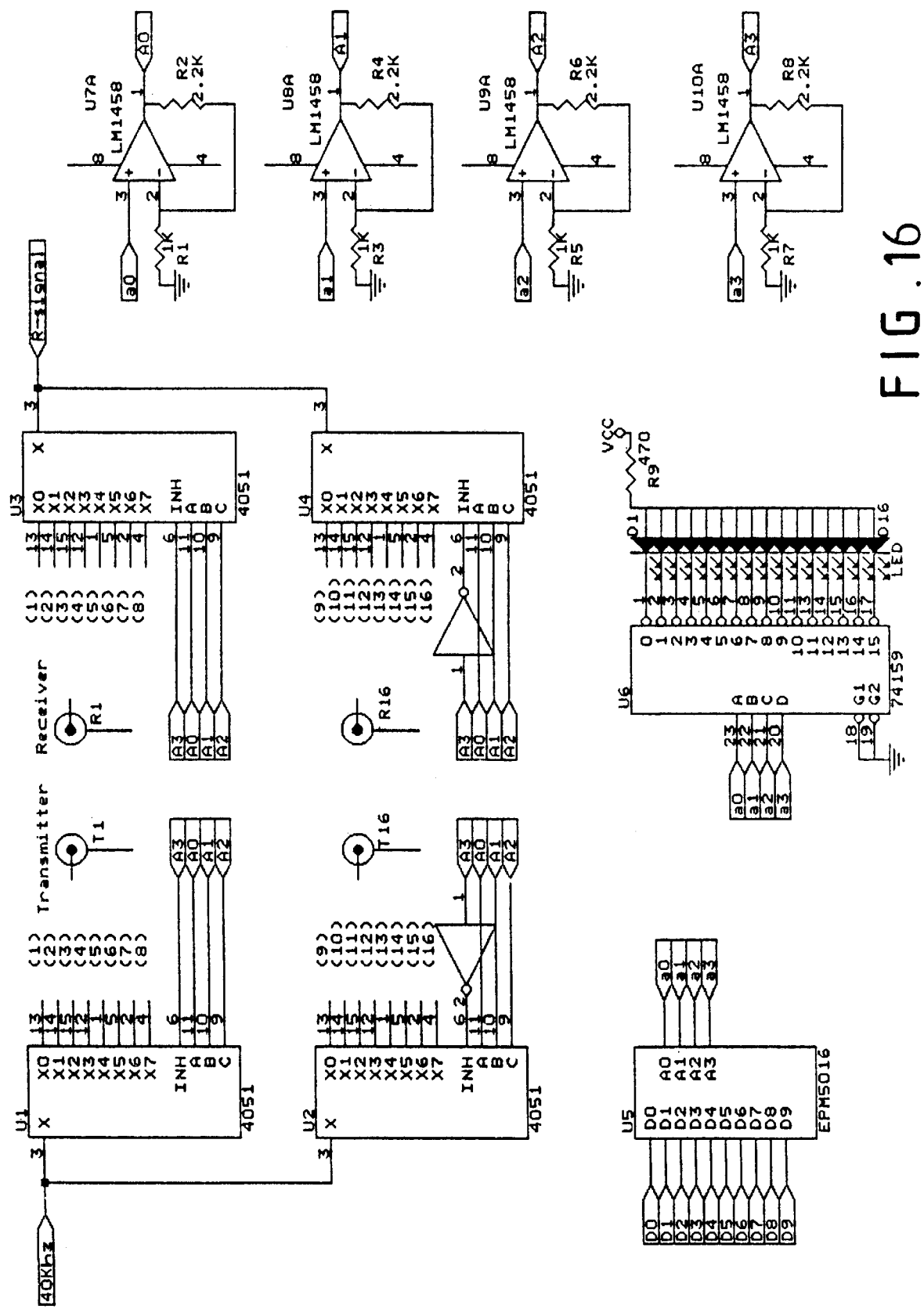
FIG. 16 is a schematic circuit diagram illustrating the interconnection of the infrared light matrix and ultrasound phase shift subsystems in the preferred embodiment of the present invention.

Referring to FIG. 16, the ultrasonic phase shift subsystem consists of an ultrasonic signal circuit, a digital phase meter and its 8751 single-chip microcomputer. Sixteen pairs of 40 kHz ultrasonic transducers are mounted on the inside wall of cover plate of the cage. One of these transducers was used to transmit ultrasound toward the animal in the cage and received the ultrasound reflected from it. An 8-bit digital phase meter was designed for detecting the phase difference between the transmitted and received ultrasonic signals. The phase meter readout the phase shift information and sends it to the 8751 single-chip microcomputer. After the processing of reconstructing the motion function from phase shift information, the output of the 8751 single-chip microcomputer is a 16-bit word data which represents the current minute motion activities of the animal. As the IR light subsystem, the 8751 single-chip microcomputer transimits the data to the decoding and interface circuits.

Figure 4:
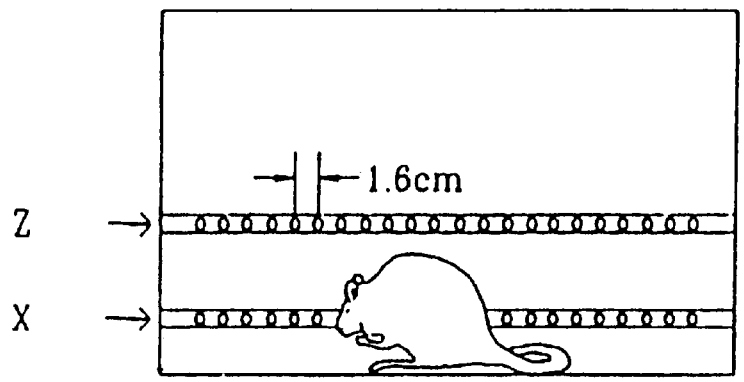
FIG. 4 is a cross-sectional elevational view of the cage in the preferred embodiment of the present invention.
Figure 5:
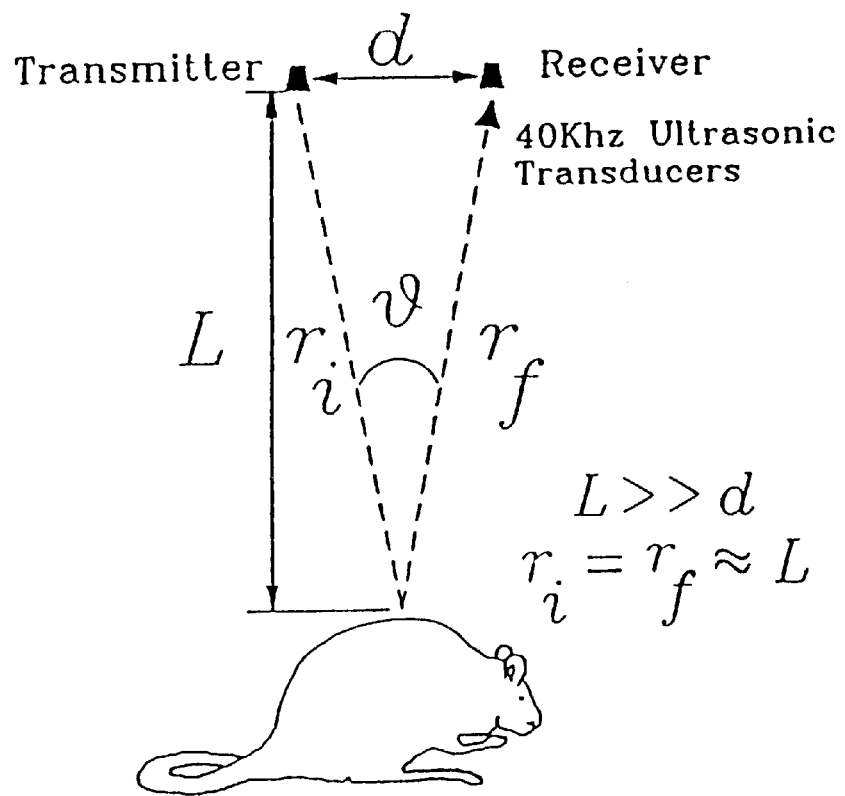
FIG. 5 is an illustrative diagram for illustrating basic principals by which activity of an animal is ultrasonically monitored in the preferred embodiment of the present invention.
Figure 9:
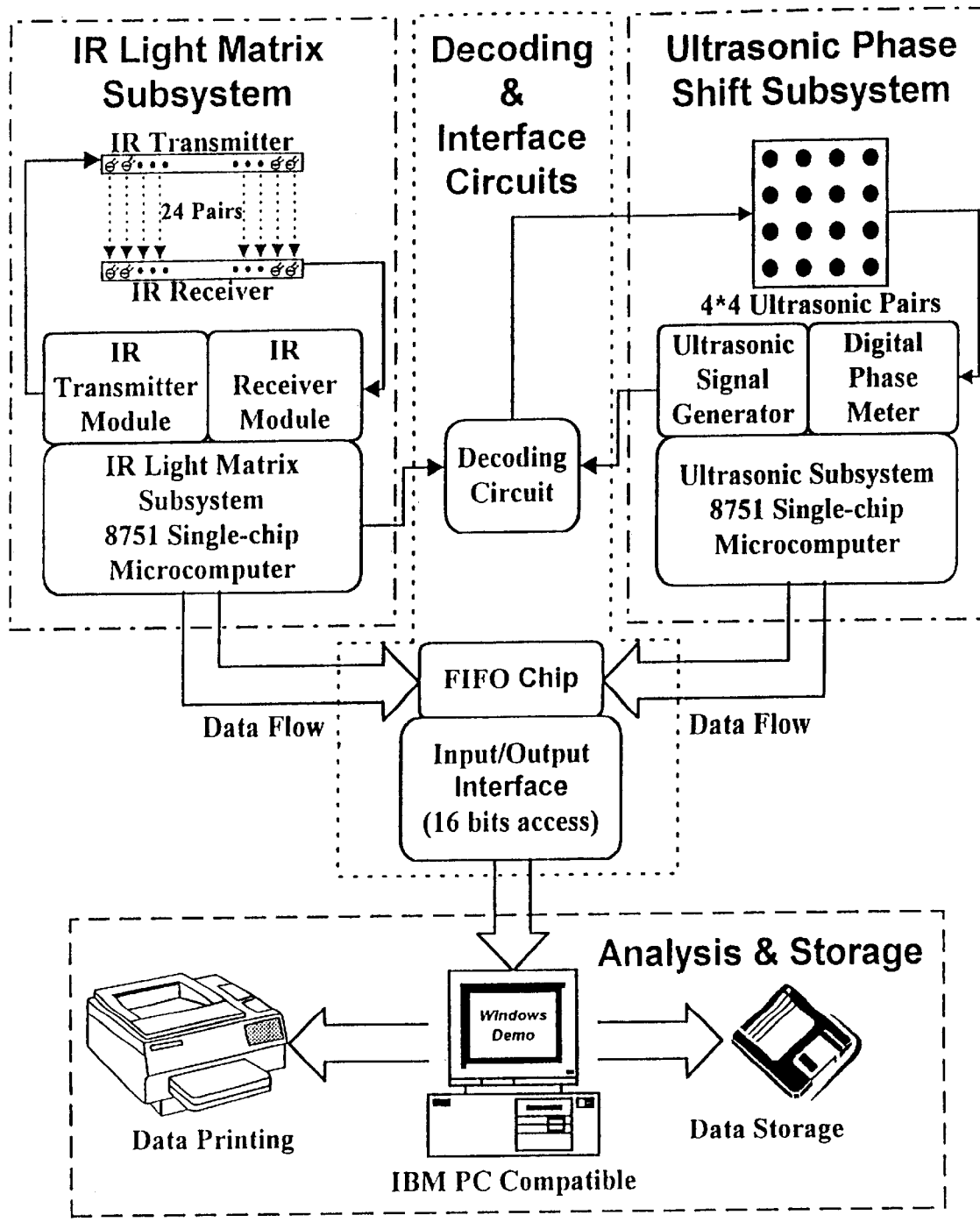
FIG. 9 is a functional diagram of the subcircuits and subsystems in the preferred embodiment of the present invention.
Figure 10:
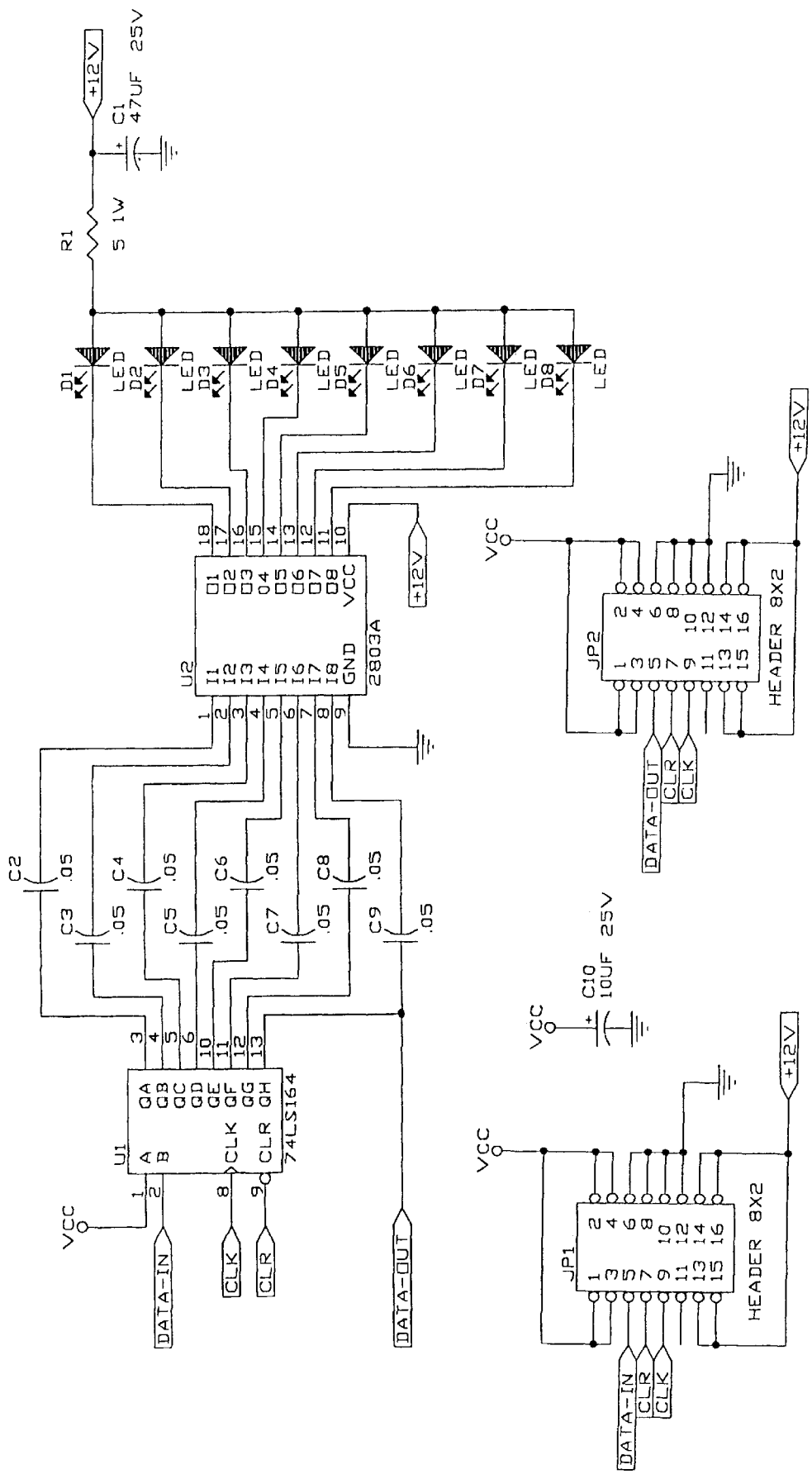
FIG. 10 is a schematic circuit diagram of the infrared ray transmitter in the preferred embodiment of the present invention.
Figure 11A:
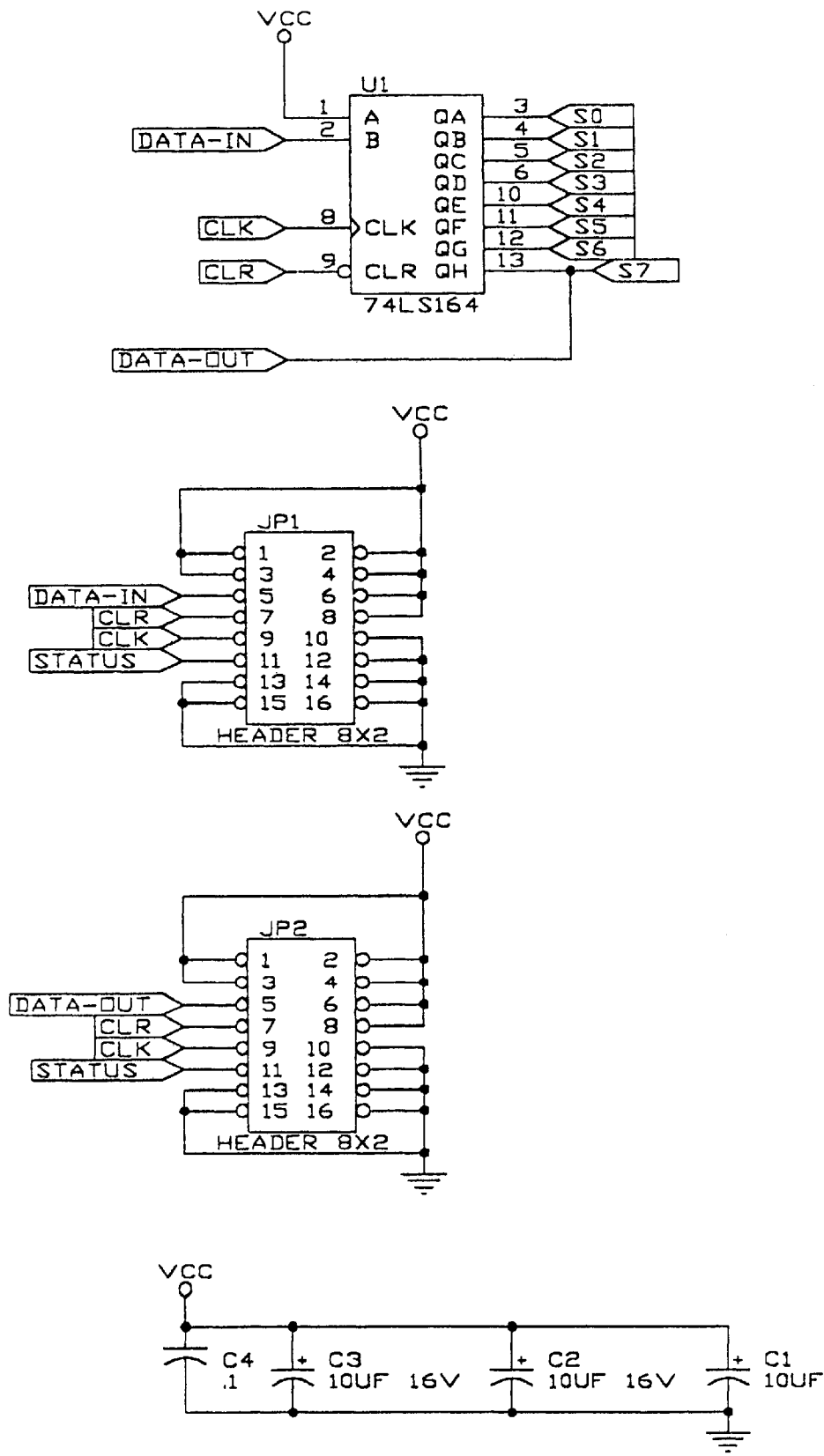
FIG. 11 is a schematic circuit diagram of an infrared ray receiver in the preferred embodiment of the present invention.
Figure 11B:
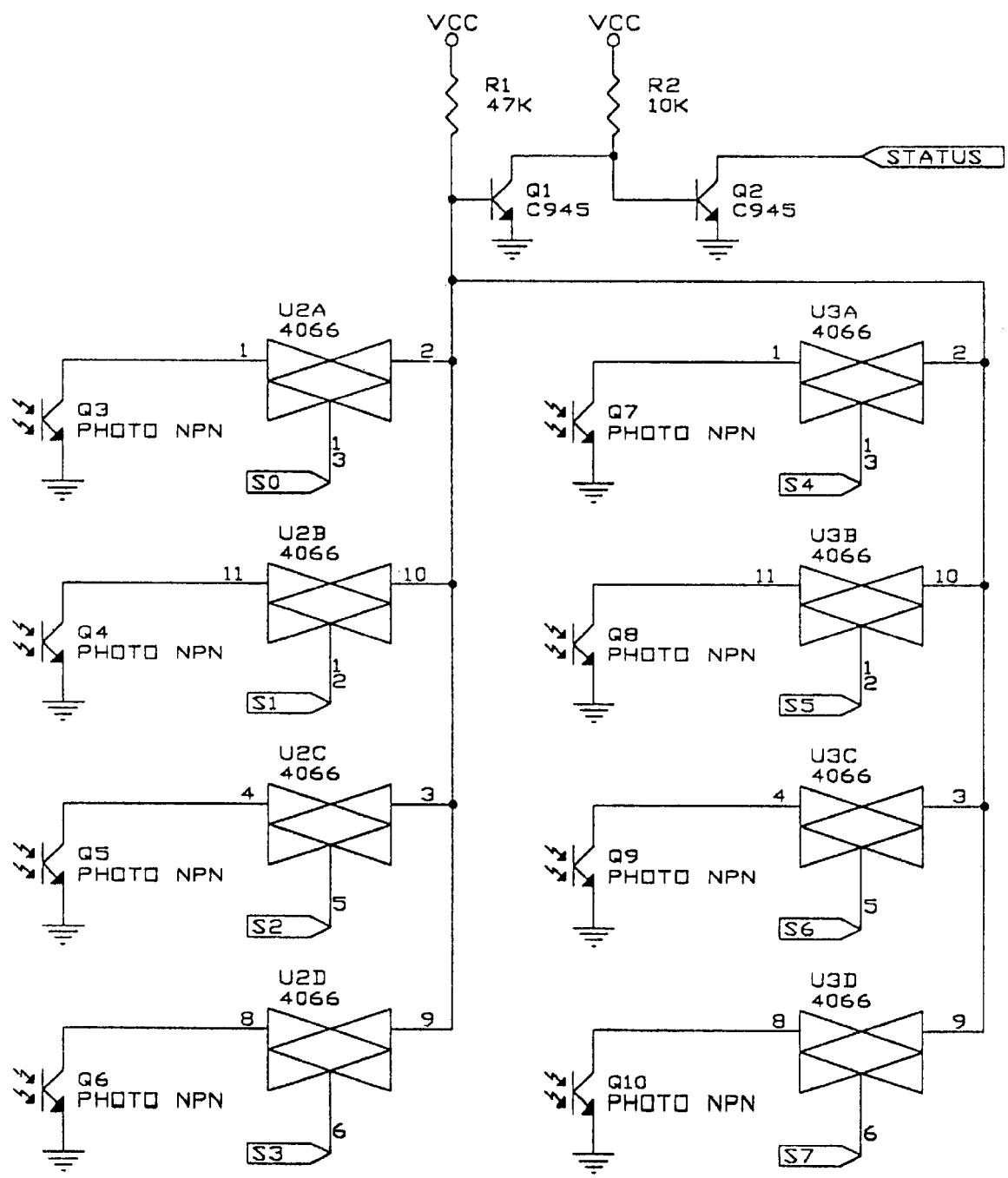

Referring also to FIG. 9, the decoding and interface circuits comprises a decoding circuit, some FIFO (First In First OUt Buffer) chips and an input/output interface. In the decoding circuit, first, we calculate the position (IRx,IRy) of the animal which is inside the cage by IR light matrix subsystem. According the position coordinate (IRx,IRy ), we select the proportional U(I,J). The proportionalbe relation between (IRx,IRy) and U(I,J) was shown in FIG. 4. For example, the position coordinate (IR3,IR16)is proportional to U(0,3). In the other words, each ultrasonic pair U(I,J) detects the small area that is about 11.25 cm long×11.25 cm wide (45 cm/4=11.25 cm). The advantage of decoded method could avoid the possible interferences among ultrasonic pairs, and increased the accuracy of the ultrasonic phase shift caused by the animal activities.

In order to acquire the data at the different sample rates from the IR light matrix subsystem (5 Hz) and the ultrasonic subsystem (100 Hz) simultaneously, the combined system uses some FIFO chips to solve the problem. Because the FIFO IC can be set at the mode of differential input and output rates, these measured data were stored in FIFO buffer and then were sent to a PC-AT computer with an I/O interface board.

DECODING AND INTERFACE CIRCUITS

The block diagram of decoding and interface circuits subsystem is shown on the middle of FIG. 9. In the decoding circuit: position coordinater acquired by the infrared light subsystem are herein decoded and the decoded data are used to control the (4*4) ultrasonic matrix on the top of the cage (refer to FIG. 16 for the circuits diagram) D0 to D4 are X-axis coordinates transmitted from the IR light matrix subsystem; D5 to D9 are Y-axis coordinater form the same. The transmitted coordinates are decoded by an IC(U5) so that control signals A0 to A3 are produced, which signals are then enlarged to become control signals with 12 voltages by U7A, U8A, U9A and U10A, which enlarged control signals are used to control four no.4051 eight-channel anolog multiplexer/demultiplexer, i.e. U1, U2, U3, U4. U1 and U2 are combined to become a demultiplexer of one to sixteen to 40 khz square wave (12 V) coming from ultrasonic sound source circuit (see FIG. 13) in order to actuate ultrasonic transmitter to emit signals to the experimented animal and then the ultrasonic receiver is used to receive the reflected signals from the animal; U3 and U4 are combined to become a multiplexer of sixteen to one, through which the above said reflected signals are sent to the digital phase meter inside ultrasonic sound source circuit for phase comparision. U6 is a decoder, which is 74159 taking one from sixteen, and is used to control the states of sixteen LED to indicate which pair of ultrasonic transmitter and receiver module is working. U5 is a decoder designed by means of PLD IC and having model no. EPM5016(see FIG. 17 for the logic circuit diagram).

An I/O interface card designed by the applicant, wherein the FIFO (first in first out) are used for the initial storage of data in order to adapt the input and output speed for the need. The data in FLFO are then sent to PC/AT computer for analysis (see FIG. 18 for the circuit diagram). I/O address is first chosen, the choosing circuit consists of four ICs, U1 to U4 and can choose address ranging from 300 h to 30 fh. The interface card need two clock speed due to the difference between the data getting speed of the IF light subsystem (5 Hz) and that of the ultrasonic phase shift subsystem (100 Hz); clock of 1 Mhz is generated by Y1 CRYSTAL; then, U5(8254IC) is set to work under working method 3, i.e. square wave generator method; counter #0 is chosen; input signal of 1 Mhz clock is transformed to become 100 Hz clock and then to become 5 Hz clock by means of U6 and U7 counters.

From the above description, it can be understood that the combined system of the present invention has following advantages.

1. Combining the IR light matrix subsystem and the ultrasonic phase shift subsystem, it could measure and analysis the animal detailed activity changes directly at a time.

2. All the subsystems are modularized so the system of the present invention can be easily maintained, assembled and expanded.

3. We could also do real time data acquisition, demo and analysis. After analyzing, and presenting the data, we could store these data in a file, or pass it to other applications for further processing or report generation.

In using the combined system to measure the animal behavior, following steps are done in sequence:

1. Put the box holding in a chosen environment or inject a chosen drug into the animal and so on, according to what knid of experiment is to be done.

2. Key in a file name for the data to be stored, a time length for the computer to run, the name and amount of the drug used. Start running the program on the computer and detect the animal behavior in conjunction with the detecting circuits.

3. The computer will analyze the acquired data after the experiment time is over.

In order to make the present invention easy to understand and implement, the hardware of the system is demonstrated with FIGS. 9, 10, 11, 12.

Figure 13A:
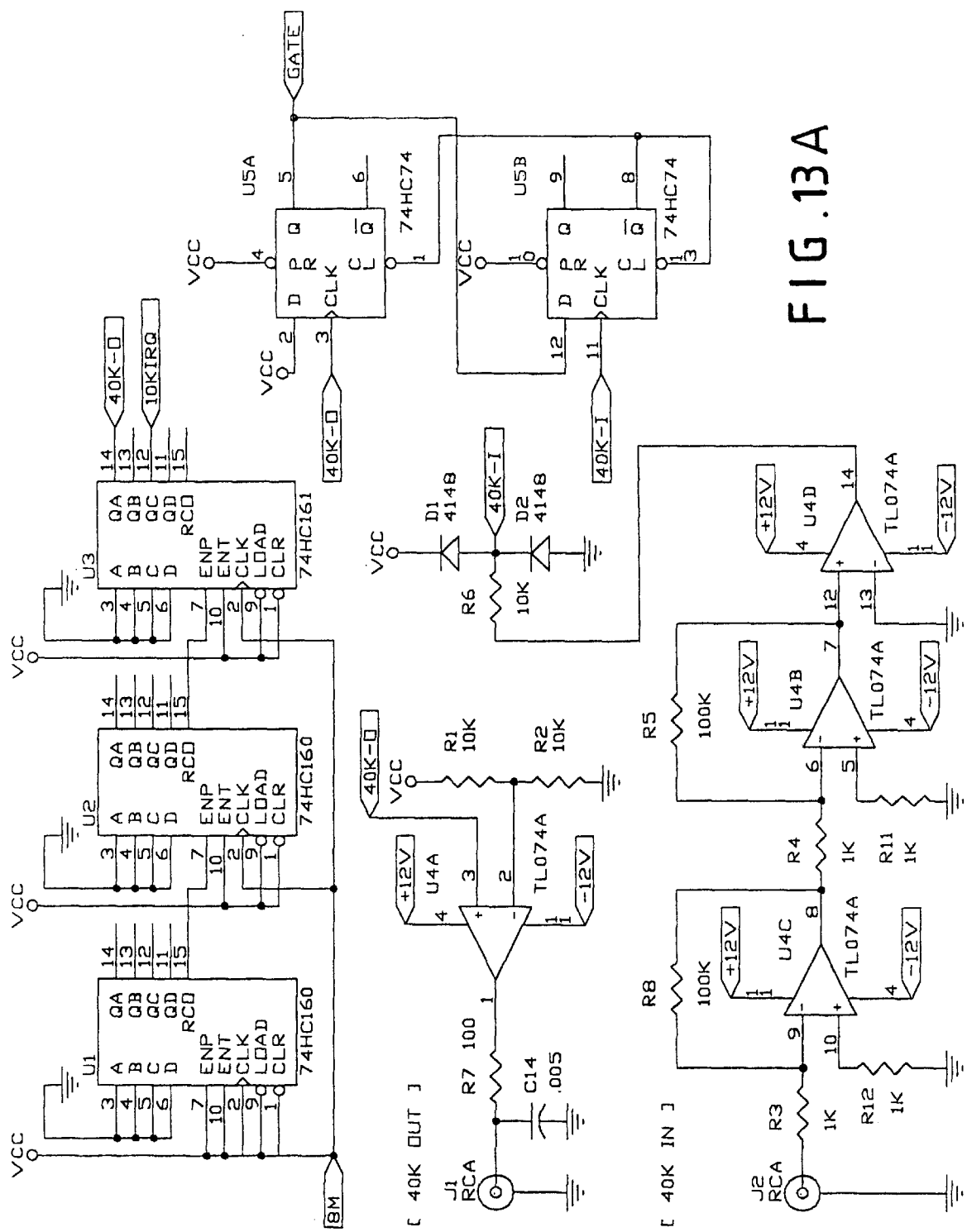
FIG. 13 is a schematic circuit diagram of the signal generator and digital phase meter circuits of the ultrasound phase shift detection subsystem in the preferred embodiment of the present inventions
Figure 13B:
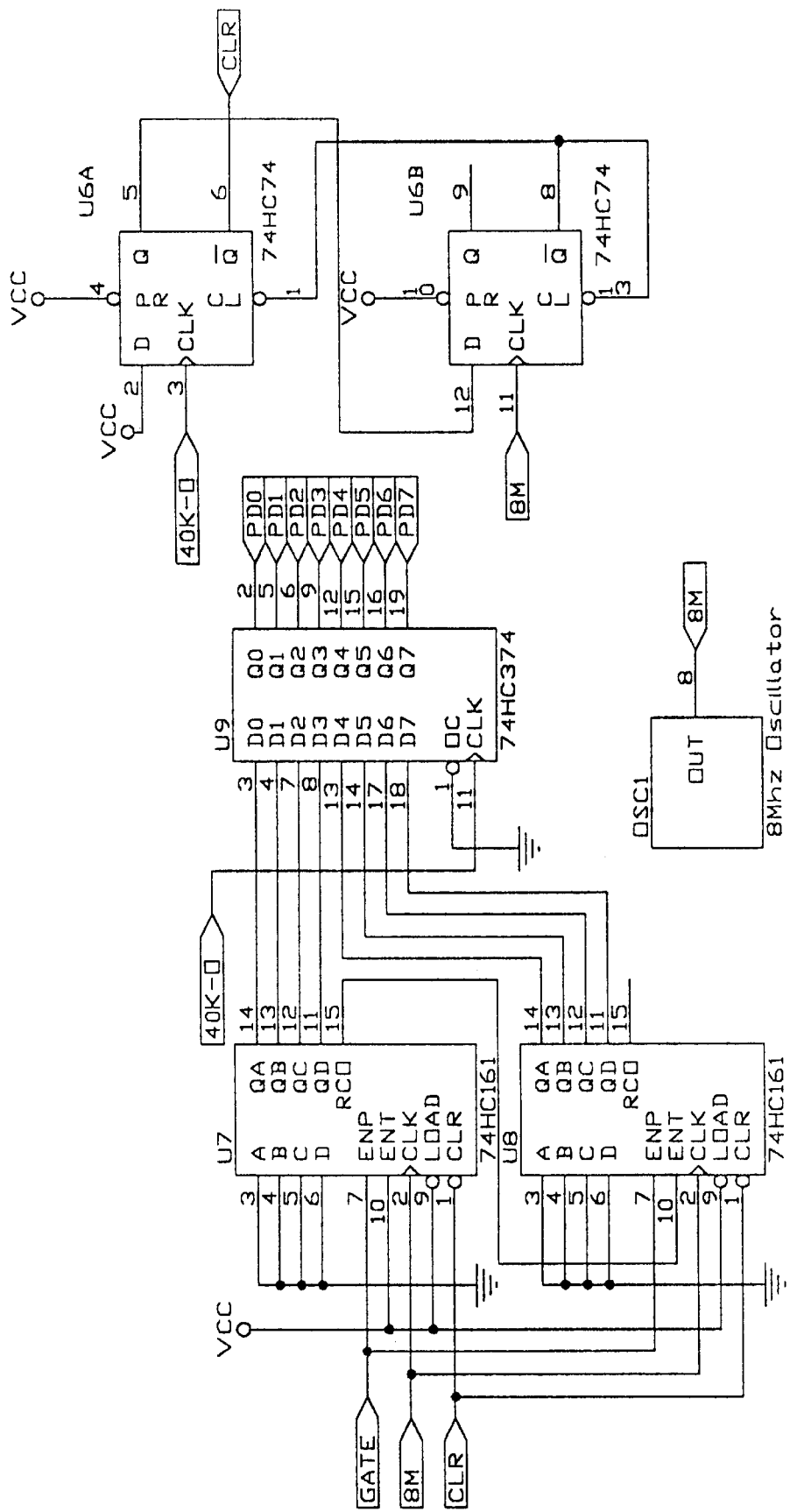
Figure 14A:
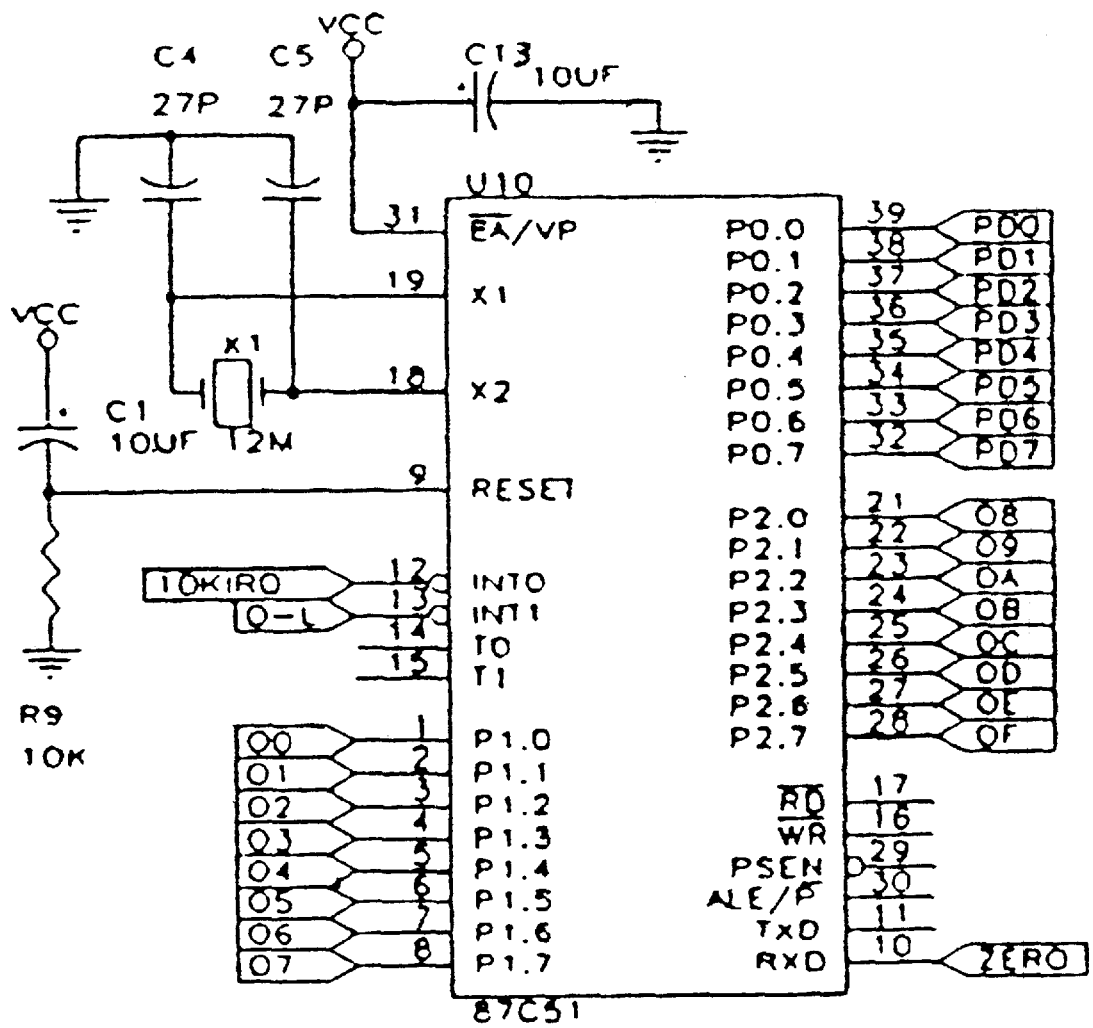
FIG. 14 is a schematic circuit diagram of the singlechip microcomputer of the ultrasound phase shift detection system in the preferred embodiment of the present invention.
Figure 14A:
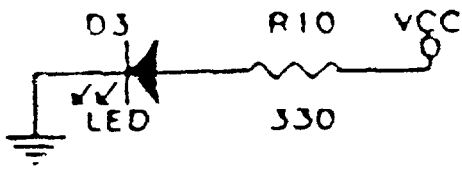
Figure 14A:
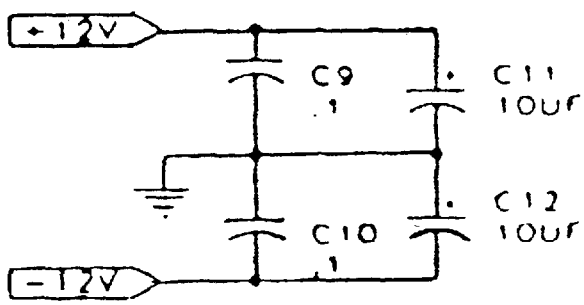
Figure 14B:
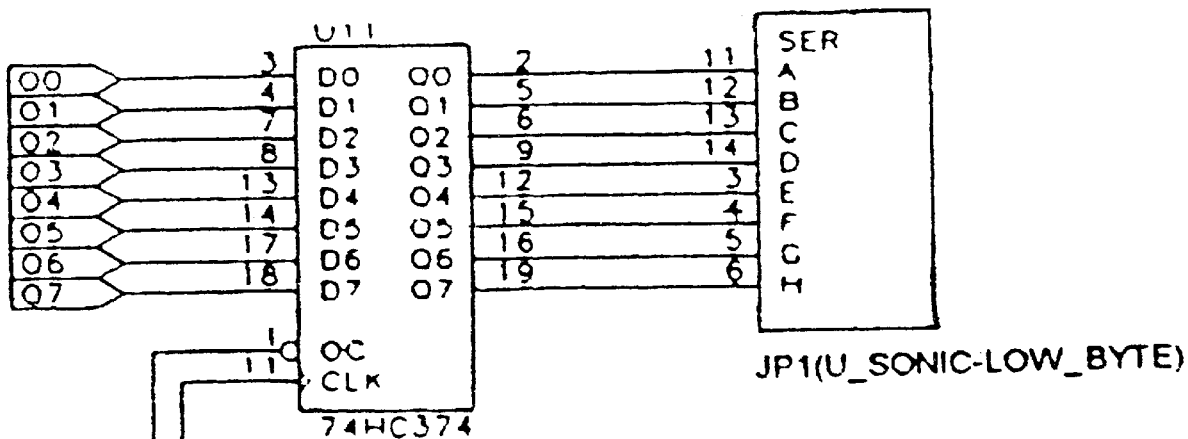
Figure 14B:
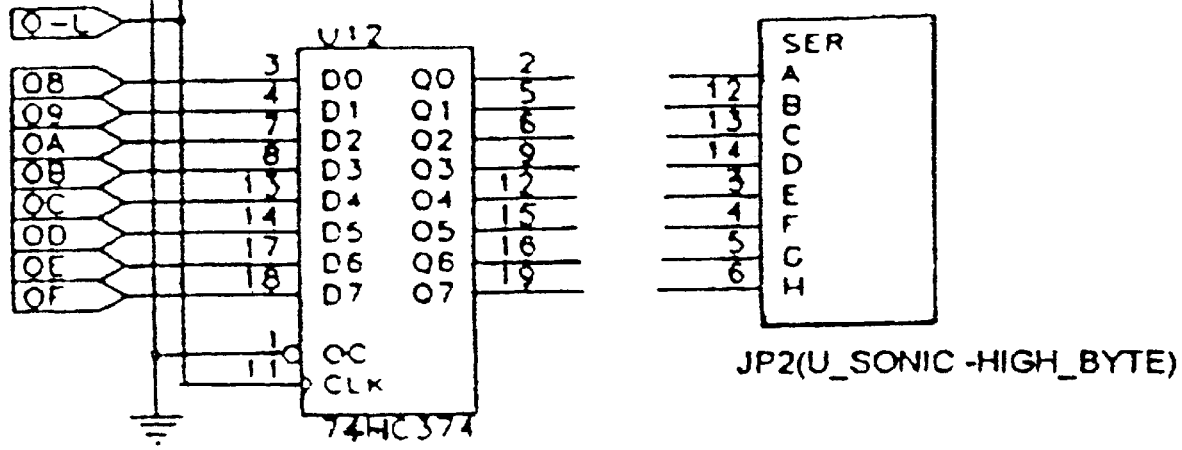
Figure 14B:
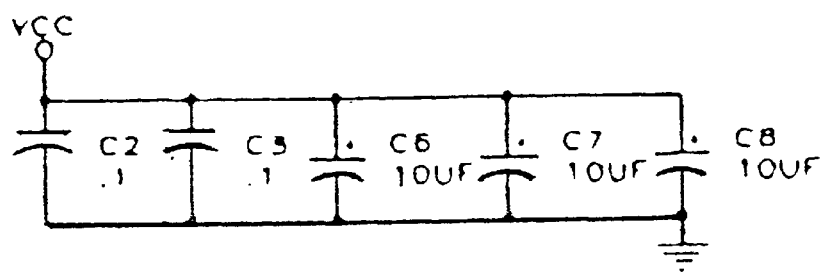

Referring to FIGS. 13 and 14, there is shown the complete circuit diagrams of the ultrasonic subsystem.

Figure 17A:
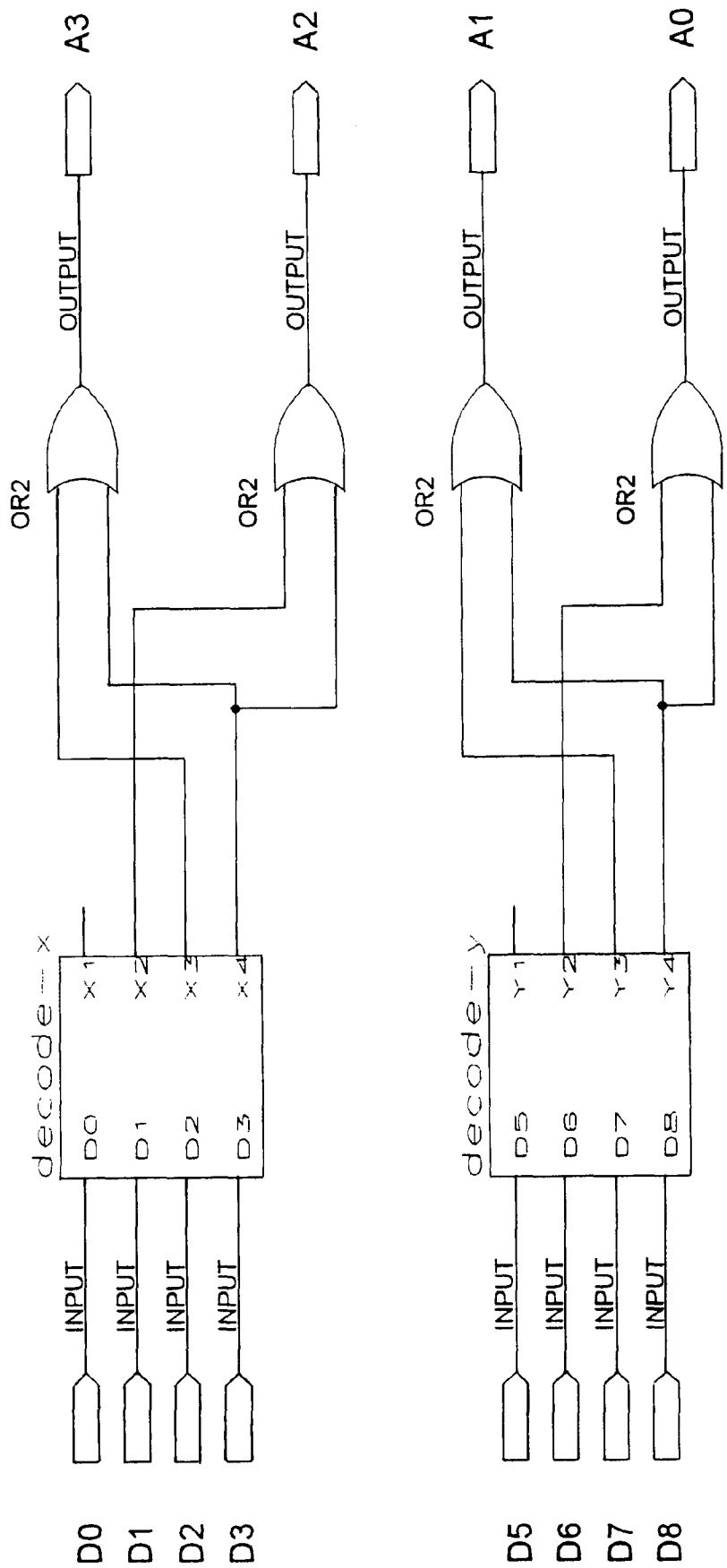
FIG. 17 is a logic diagram of the decoder in the preferred embodiment of the present invention, and, FIG. 18 is a schematic circuit diagram of the input/output interface in the preferred embodiment of the present invention.
Figure 17B:
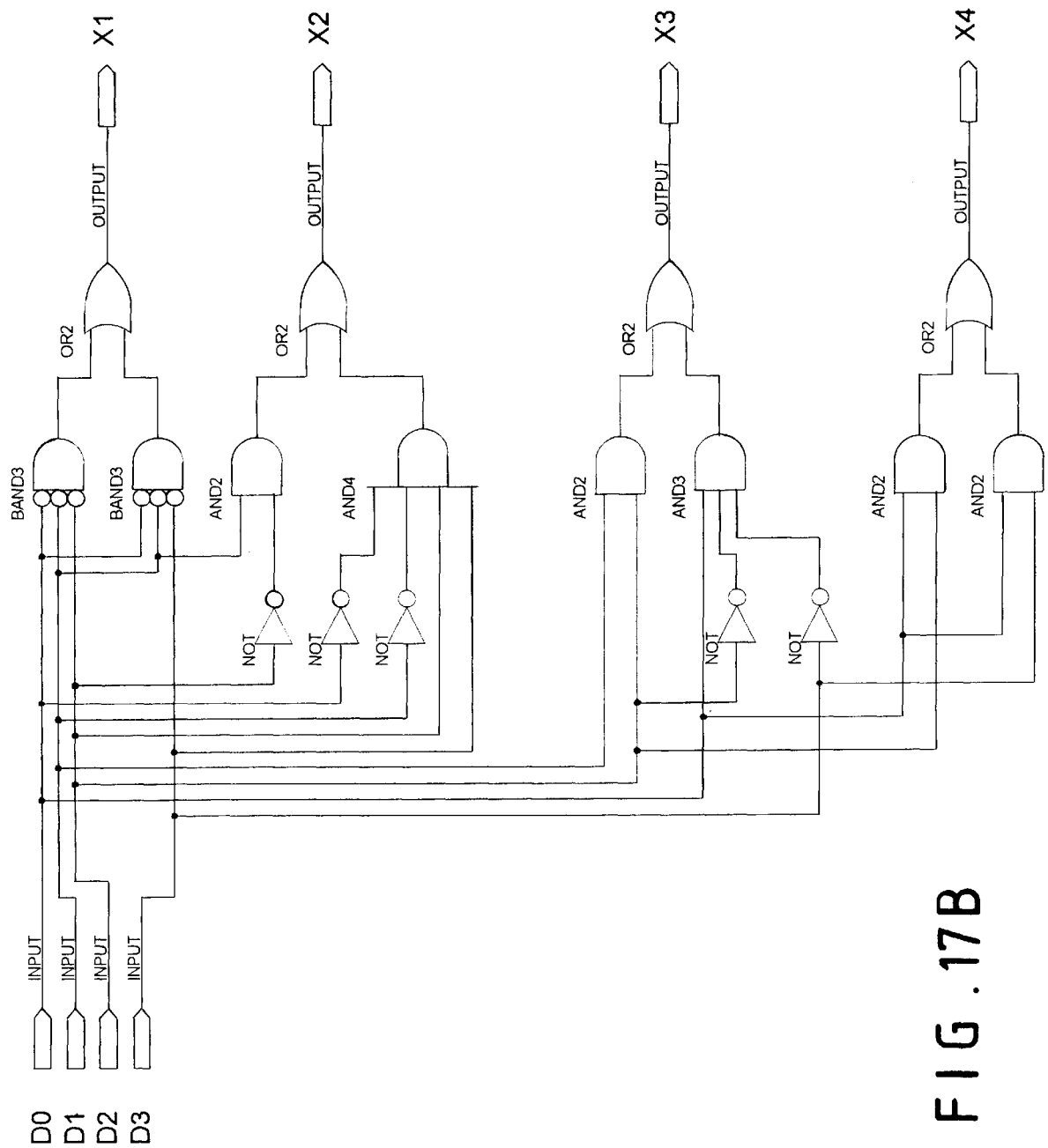
Figure 17C:
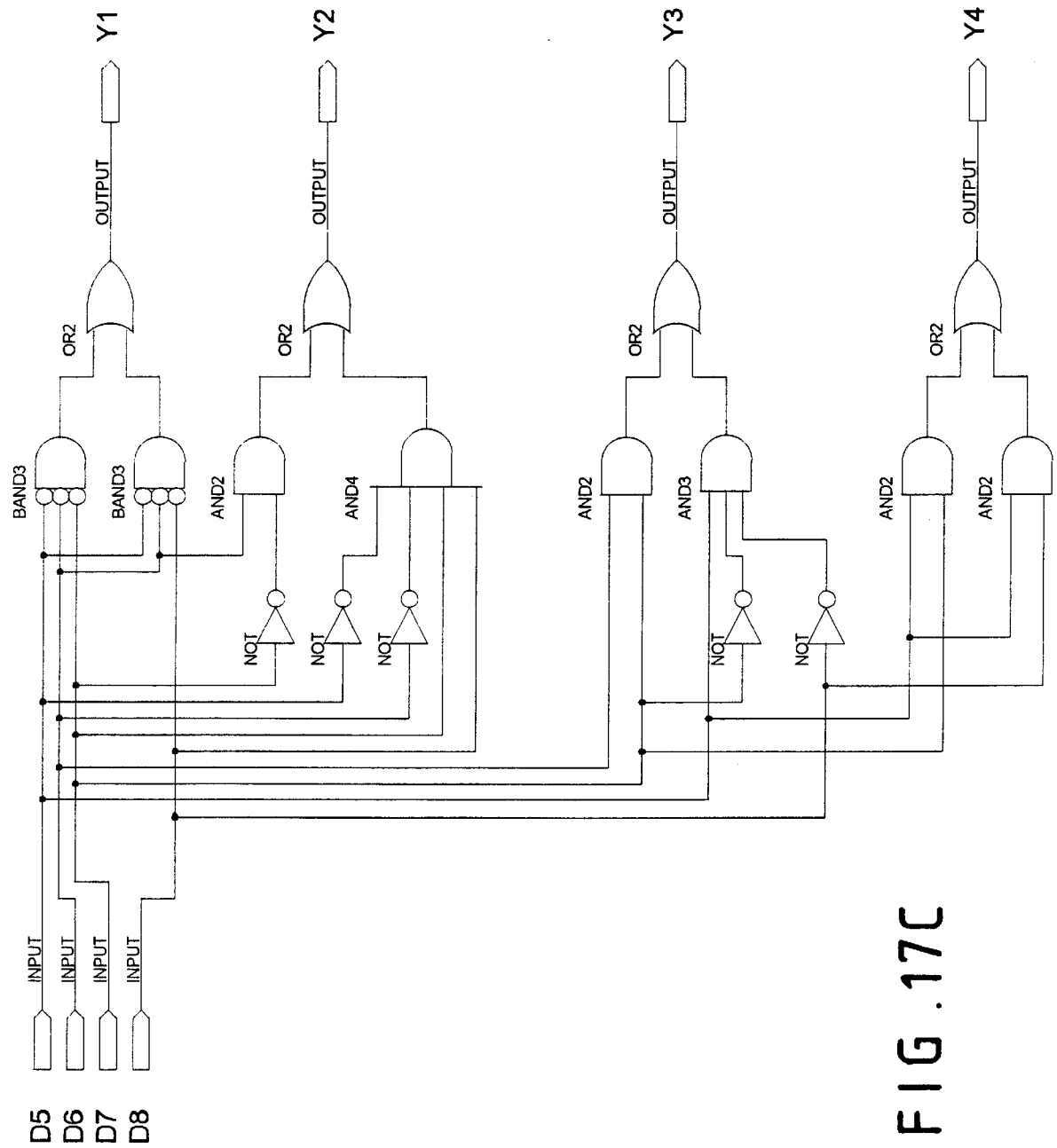

The decoding subsystem decodes the position of the animal acquired by the infrared light subsystem and accordingly by control the ultrasonic subsystem. The circuit diagram of the decoding subsystem is shown in FIG. 16, and the logic circuit diagram of US, a decoder with model number EPM5016 and designed by a PLD IC, is shown in FIG. 17.

Figure 12A:
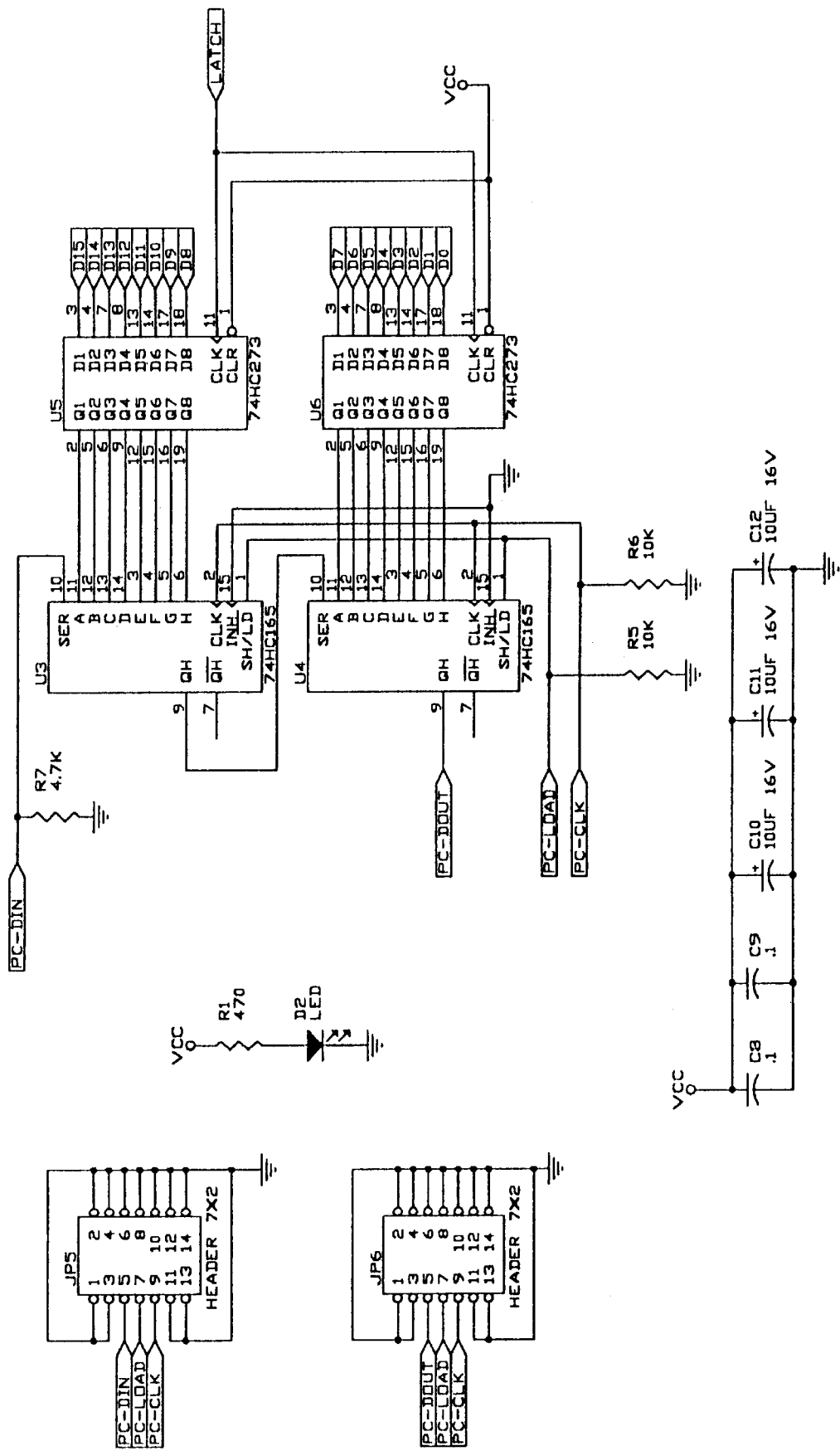
FIG. 12 is a schematic circuit diagram of the signal generator and digital phase meter of the ultrasound phase shift detection subsystem in the preferred embodiment of the present invention
Figure 12B:
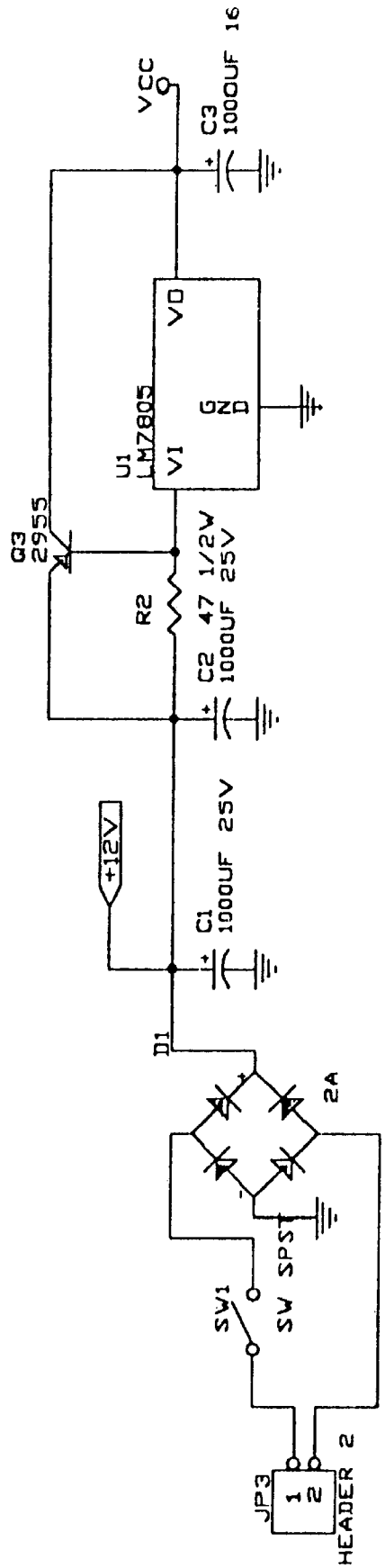
Figure 12C:
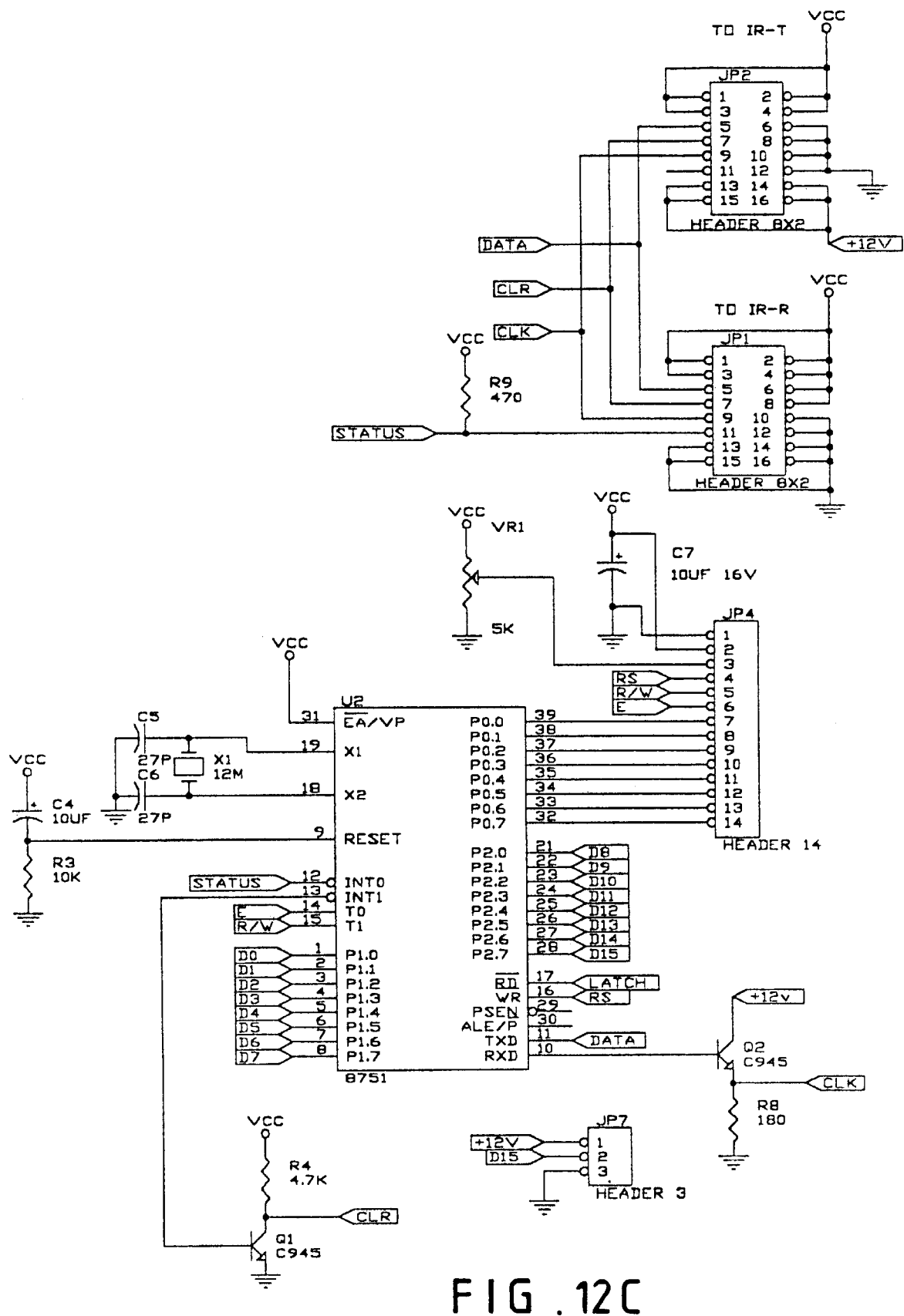
Figure 18A:
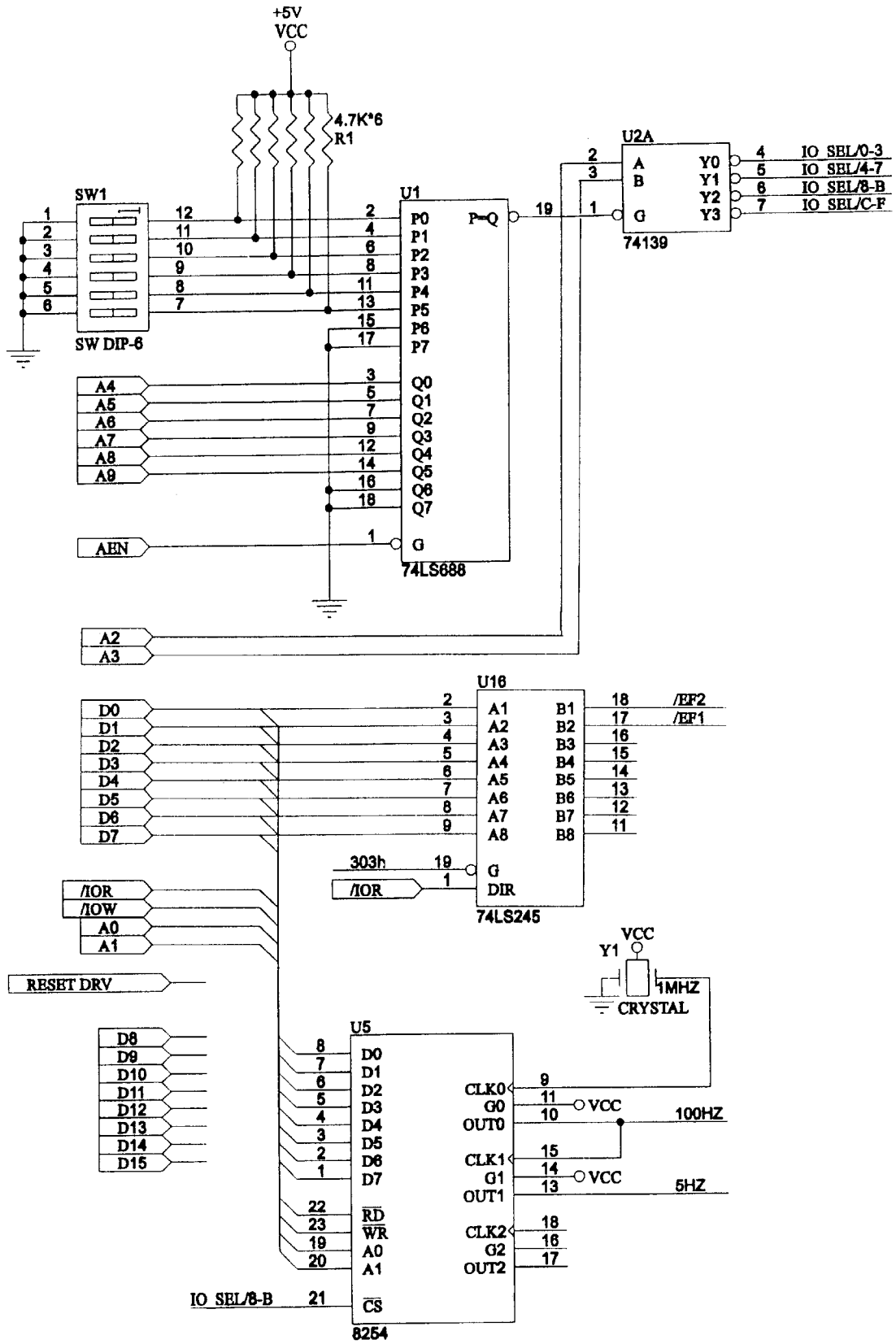
Figure 18B:
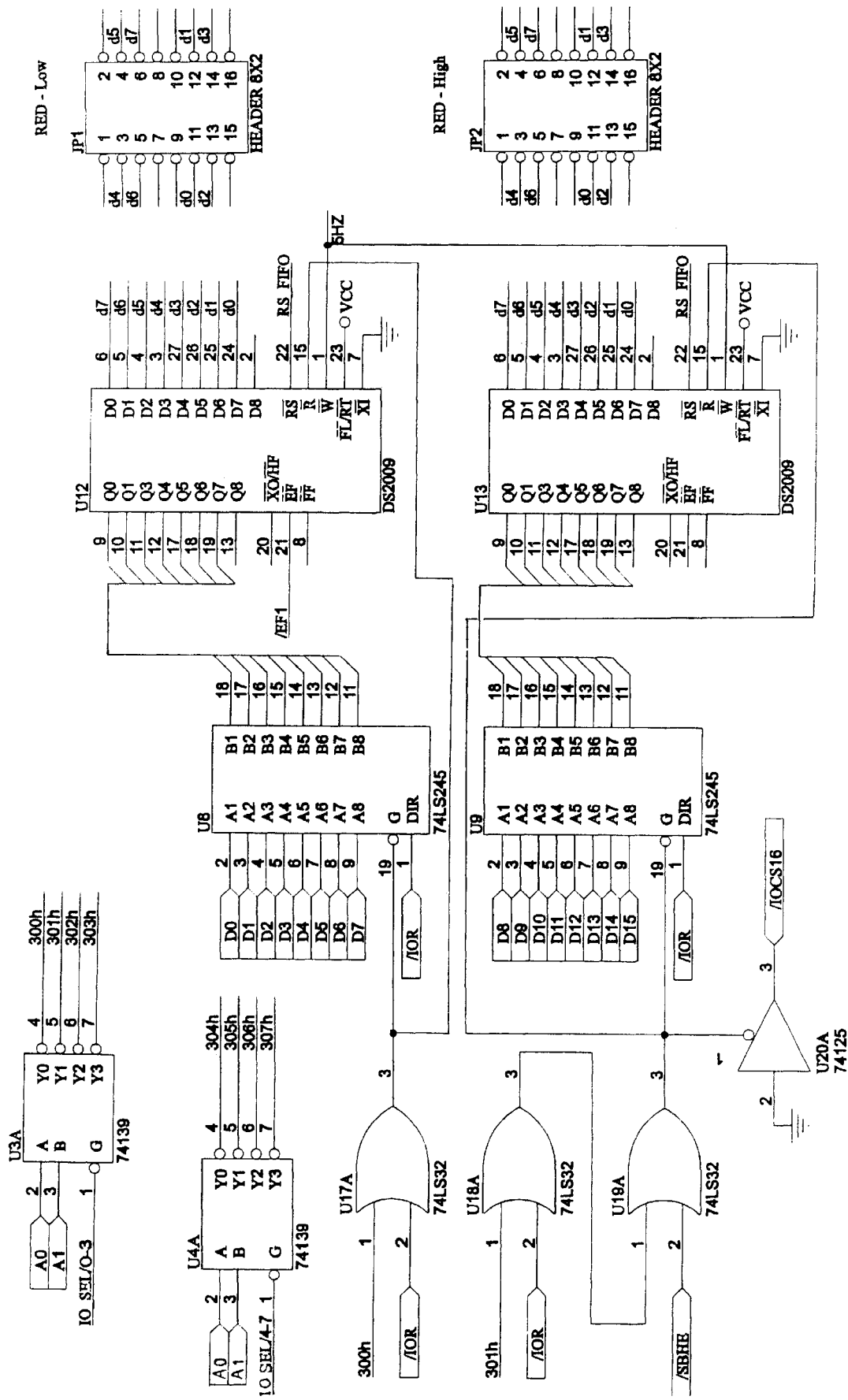
Figure 18C:
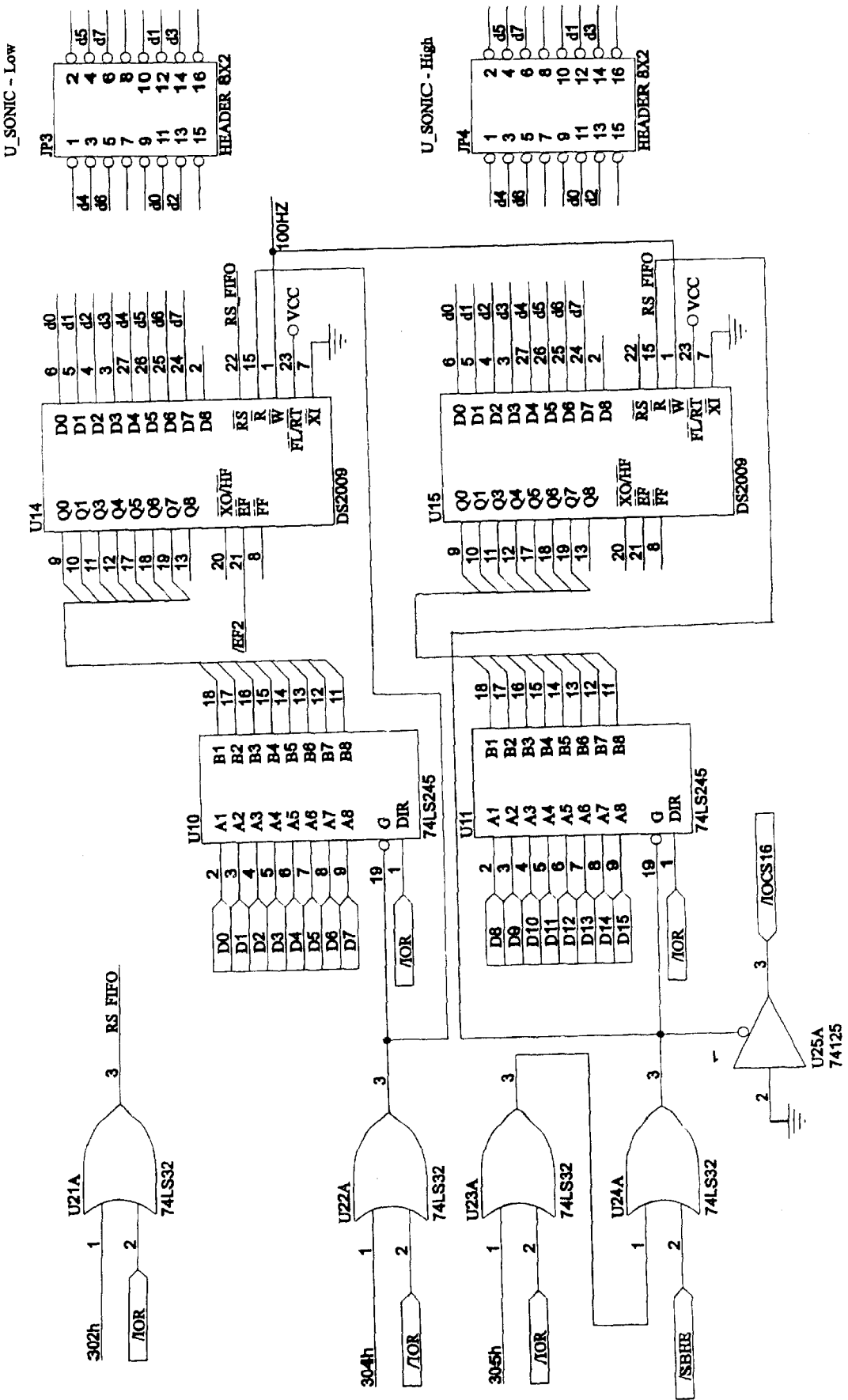

The 16 bits of the interface circuit and FIFO interface circuit of the present invention is shown in FIG. 18, wherein JPI(red-low-byte) connects with JPS of FIG. 12; FP2(red-high-byte) connects with JP6 of FIG. 12; JP3(U-sonic-low-byte) connects with JP1 of FIG. 14; JP4(U-sonic-high-byte) connects with JP2 of FIG. 14. U12, U13, U14, U15 are FIFO chips(model no.DS2009) made by Dallas company. Red-low-byte is stored in U12, red-high-byte in U13, U-sonic-low-byte in U14, U-sonic-high byte in U15. 5 Hzclock controls the input speed of U12 and U13 while 100 Hz clock controls the input speed of U14 and U15. The data stored in U12 and U13 are passed into the computer through two Latch IC 74245, U8 and U9 by means of 16 bits I/O method. The data stored in U14 and U15 are passed into the computer through two latch IC 74245, U10 and U11 by means of 16 bits I/O method.

The IC(U121A) is used to reset four FIFO chips one time during reading period of address 302 h. U16 is used to send EF1 and EF2 to the computer wherein EF1 judges whether FIFO U12 and U13 are empty and EF2 judge whether FIFO U14 and U15 are empty.

From the above, it can be understood that the present invention has following advantages:

1. The system of the present invention combines the infrared light matrix subsystem and the ultrasonic subsystem, has the advantages of both and thus can precisely record slight change of the position and the behavior of the animal, having great contribution for the animal behavior research.

2. The whole system is formed to have simple framework and all the subsystems are each designed to be a module resulting in the advantange that the hardware of this combined system will be flexible, easily-expanded and easily-maintained.

3. The use of computer for data acquirement, storage, analysis and display makes the operation more convenient and the result comes out faster because the computer runs synchronously along with the experiment.

While the preferred embodiments of the invention have been described above, it will be recognixed and understood that various modifications may be made therein and the appended claims are intended to cover all such modifications which may fall within the spirit and scope of the invention.

What is claimed is:

1. A system for automatically sensing the activities of an animal within a confined space comprising:

(a) a containment assembly adapted to confine said animal therein, said containment assembly having at least a top portion and a plurality of side portions;

(b) an infrared light matrix subsystem including a plurality of infrared transmitter and receiver pairs attached to said side portions of said containment assembly and a single chip microcomputer coupled thereto, said infrared light matrix subsystem single chip microcomputer controlling said infrared transmitter and receiver pairs to sense the position of said animal relative to a first plane;

(c) an ultrasonic phase shift subsystem including a plurality of ultrasonic transmitter and receiver pairs attached to said top portion of said containment assembly and a single chip microcomputer coupled thereto, said ultrasonic phase shift subsystem single chip microcomputer controlling said ultrasonic transmitter and receiver pairs to sense the position change of said animal relative to a second plane; and, (d) a decoding circuit subsystem coupled to said infrared light matrix and said ultrasonic phase shift subsystems; and, (e) an interface circuit subsystem coupled to said infrared light matrix and said ultrasonic phase shift subsystems for input and output therethrough of data of said system.

2. The system for sensing the activities of an animal within a confined space as recited in claim 1 wherein said infrared light matrix subsystem further includes a transmitter module and a receiver module, said transmitter module actuating said infrared transmitters, said receiver module receiving output signals from said infrared receivers.

3. The system for sensing the activities of an animal within a confined space as recited in claim 1 wherein said ultrasonic phase shift subsystem further includes a signal generator circuit and a digital phase meter, said signal generator circuit producing ultrasonic sound signals, said digital phase meter detecting phase differences between incident ultrasonic waves transmitted from said ultrasonic transmitters and reflected waves received by said ultrasonic receivers.

4. The system for sensing the activities of an animal within a confined space as recited in claim 1 wherein said decoding circuit subsystem includes a multiplexer and a demultiplexer, said multiplexer and said damultiplexer cooperatively selecting for actuation at least one of said ultrasonic transmitter and receiver pairs responsive to signals received from said infrared light matrix subsystem.

5. The system for sensing the activities of an animal within a confined space as recited in claim 1 wherein said interface circuit subsystem includes a plurality of first-in-first-out buffer chips, said first-in-first-out buffer chips receiving signals from said infrared light matrix subsystem and said ultrasonic phase shift subsystem.

6. The system for sensing the activities of an animal within a confined space as recited in claim 5 wherein said interface circuit subsystem includes means for reversibly transmitting 16-bit data signals to a computer.

* * * * *